US012582670B2

(12) United States Patent
Grossman et al.

(10) Patent No.: US 12,582,670 B2
(45) Date of Patent: Mar. 24, 2026

(54) LIGNIN SOLVATION USING AQUEOUS BIOLOGICALLY COMPATIBLE BUFFERS

(71) Applicant: University of Florida Research Foundation, Incorporated, Gainesville, FL (US)

(72) Inventors: Adam B. Grossman, Gainesville, FL (US); Kelly C. Rice, Gainesville, FL (US); Willem Evert Vermerris, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 924 days.

(21) Appl. No.: 17/421,880

(22) PCT Filed: Jan. 10, 2020

(86) PCT No.: PCT/US2020/013061
§ 371 (c)(1),
(2) Date: Jul. 9, 2021

(87) PCT Pub. No.: WO2020/146720
PCT Pub. Date: Jul. 16, 2020

(65) Prior Publication Data

US 2022/0096533 A1 Mar. 31, 2022

Related U.S. Application Data

(60) Provisional application No. 62/815,778, filed on Mar. 8, 2019, provisional application No. 62/791,345, filed on Jan. 11, 2019.

(51) Int. Cl.

| | |
|---|---|
| ***A61K 31/775*** | (2006.01) |
| ***A61K 31/7072*** | (2006.01) |
| ***A61P 31/04*** | (2006.01) |
| ***C07G 3/00*** | (2006.01) |

(52) U.S. Cl.
CPC ........ *A61K 31/775* (2013.01); *A61K 31/7072* (2013.01); *A61P 31/04* (2018.01); *C07G 3/00* (2013.01)

(58) Field of Classification Search
CPC .................................. A61P 31/04; C07G 3/00
See application file for complete search history.

(56) References Cited

U.S. PATENT DOCUMENTS

| | | | | |
|---|---|---|---|---|
| 9,765,478 B2 | 9/2017 | Brandt et al. | | |
| 2010/0279372 A1* | 11/2010 | Cho | C12P 7/10 | 435/165 |
| 2018/0370924 A1 | 12/2018 | Beghetto | | |

FOREIGN PATENT DOCUMENTS

| | | | |
|---|---|---|---|
| WO | WO-2014/159558 A1 | 10/2014 | |
| WO | WO-2017179016 A1 * | 10/2017 | A01N 61/00 |

OTHER PUBLICATIONS

Lundquist, K., et al. Arch. Microbiol. 1977, 112, 291-296. (Year: 1977).*
Alzagameem, A., et al. Polymers. Nov. 2019, 670. (Year: 2019).*
What is a Good's Buffer?. Hopax Fine Chemicals. HOPAX. Web. pp. 1-7. (Year: 2019).*
Kim, J. S., et al. Bioresource Technology. 199, 2016, 42-48. (Year: 2016).*
Whitehead, T. A., et al. ACS Sustainable Chem. Eng. May 2017, 6247-6252 . . . (Year: 2017).*
Whitehead, T. A., et al. ACS Sustainable Chem. Eng. 2017, Supporting information. (Year: 2017).*
Hopax Fine Chemicals. 8 uses of MOPS buffer you didn't know—Blog. Oct. 19, 2018. pp. 1-7. Web. (Year: 2018).*
Melro, E. et al. International Journal of Biological Macromolecules. 148 (2020) 688-695. (Year: 2020).*
Xu, Z., et al. Journal of Bioresources and Bioproducts 8 (2023) 461-477. (Year: 2023).*
Saadan, R., et al. Environ. Earth Sci. Proc. Mar. 31, 2024. (Year: 2024).*
"Alkaline." Merriam-Webster.com Dictionary, Merriam-Webster, https://www.merriam-webster.com/dictionary/alkaline. Accessed Apr. 7, 2025. (Year: 2025).*
International Searching Authority, International Search Report and Written Opinion for International Application No. PCT/US2020/013061, dated Jan. 10, 2020, (10 pages), United States Patent and Trademark Office, USA.
Vishtal, Alexey et al. *Challenges In Industrial Applications Of Technical Lignins*, BioResources, vol. 6, No. 3, pp. 3547-3568.
Johansson, Kristin et al. *Comparison Of Lignin Derivatives As Substrates For Laccase-Catalyzed Scavenging Of Oxygen In Coatings and Films*, Journal of Biological Engineering, vol. 8, No. 1, Dec. 2014, pp. 1-10.

* cited by examiner

*Primary Examiner* — Andrea Olson
*Assistant Examiner* — Samuel L Galster
(74) *Attorney, Agent, or Firm* — Alston & Bird LLP

(57) ABSTRACT

Provided are aqueous lignin solutions containing lignin solvated in Good's Buffers. The aqueous lignin solutions can be used in a variety of applications including biomedical research and in manufacturing a variety of lignin containing products including food grade and biomedical products. The aqueous lignin solutions can also be used in the treatment of microbial infection, as an adjuvant in antimicrobial therapeutics or therapy, and in forming antimicrobial products. Methods of making and using aqueous lignin solutions are also described.

20 Claims, 17 Drawing Sheets

A. *S. aureus* UAMS-1 TSA

Oxacillin 0.2 µg Amoxicillin 2 µg Ampicillin 2 µg Penicillin 2 µg

B. *S. aureus* UAMS-1 TSA + 5mg/mL lignin

Oxacillin 0.2 µg Amoxicillin 2 µg Ampicillin 2 µg Penicillin 2 µg

A.

A.

B.

A.

B.

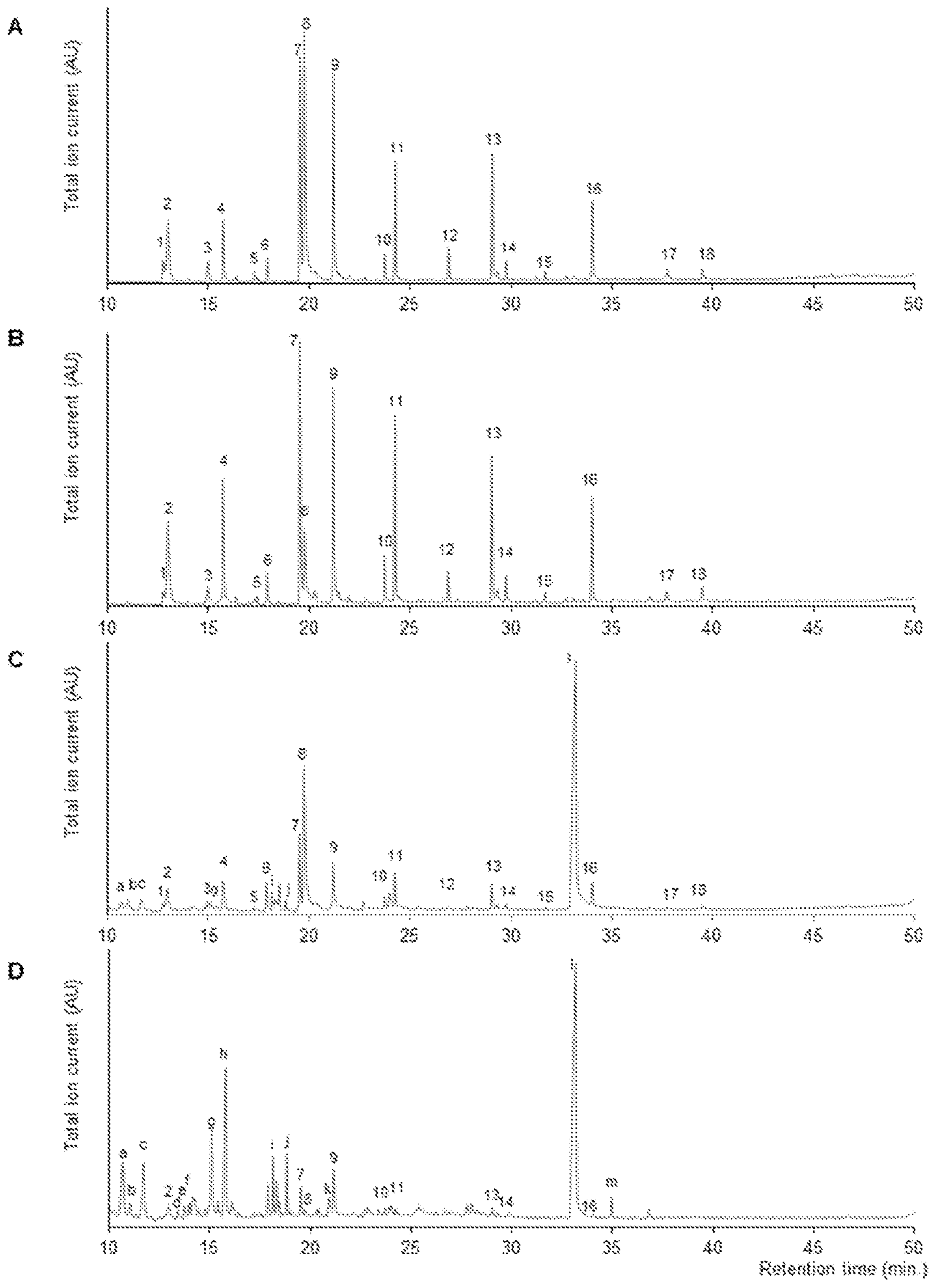
FIG. 20A-D

| Peak | Retention time (RT) (min) | Diagnostic m/z values | Compound | Origin |
|---|---|---|---|---|
| 1 | 12.7 | 94, 66 | phenol | lignin |
| 2 | 13.0 | 124, 109, 81 | guaiacol | lignin |
| 3 | 15.0 | 108, 107, 77 | 4-methylphenol | lignin |
| 4 | 15.8 | 138, 123, 95 | 4-methylguaiacol | lignin |
| 5 | 17.2 | 122, 107, 77 | 4-ethylphenol | lignin |
| 6 | 17.9 | 152, 137 | 4-ethylguaiacol | lignin |
| 7 | 19.6 | 150, 135 | 4-vinylguaiacol | lignin |
| 8 | 20.1 | 120, 91 | 4-vinylphenol | lignin |
| 9 | 21.2 | 154, 139, 111 | 2,6-dimethoxyphenol | lignin |
| 10 | 23.7 | 164, 149, 131 | trans-iso-eugenol | lignin |
| 11 | 24.3 | 168, 153, 125 | 2,6-dimethoxy-4-methylphenol | lignin |
| 12 | 26.9 | 182, 167 | 4-ethyl-2,6-dimethoxyphenol | lignin |
| 13 | 29.1 | 180, 165, 137 | 2,6-dimethoxy-4-vinylphenol | lignin |
| 14 | 29.8 | 194, 167, 91 | 2,6-dimethoxy-4-(2-propenyl)-phenol | lignin |
| 15 | 31.7 | 194, 119, 91 | 2,6-dimethoxy-4-(prop-1-en-1-yl)-phenol | lignin |
| 16 | 34.0 | 194, 119, 91 | 2,6-dimethoxy-4-(prop-1-en-1-yl)-phenol | lignin |
| 17 | 37.8 | 196, 181 | acetosyringone | lignin |
| 19 | 39.5 | 210, 167 | sinapyl alcohol | lignin |
| a | 10.7 | 84, 55 | (5H)-furan-2-one | polysaccharides |
| b | 11.0 | 114, 85, 58 | 4-hydroxy-5,6-dihydro-(2H)-pyran-2-one | polysaccharides |
| c | 11.7 | 112, 84, 69 | 2-hydroxy-3-methyl-2-cyclopenten-1-one | polysaccharides |
| d | 13.4 | 82, 81, 53 | 2,2-[oxybis(methylene)]bis-furan | polysaccharides |
| e | 13.7 | 126, 95 | furyl hydroxymethylketone | polysaccharides |
| f | 14.0 | 126, 83, 69 | 3-ethyl-2-hydroxy-2-cyclopenten-1-one | polysaccharides |
| g | 15.1 | 85, 57 | unknown | unknown |
| h | 15.7 | 57 | unknown | unknown |
| i | 18.1 | 114, 84, 71 | dihydrohydroxypyran-1-one | polysaccharides |
| j | 18.8 | 69, 57 | di-anhydro-alpha-D-glucopyranose | polysaccharides |
| k | 20.9 | 126, 97, 69 | 5-hydroxymethylfurfural | polysaccharides |
| l | 33.0 | 73, 60 | 1,6-anhydro-beta-D-glucopyranose | polysaccharides |
| m | 34.9 | 95, 71, 58 | 6,10,14-trimethyl-2-pentadecanone | chlorophyll |

FIG. 20E

A. No lignin (90,000× magnification)
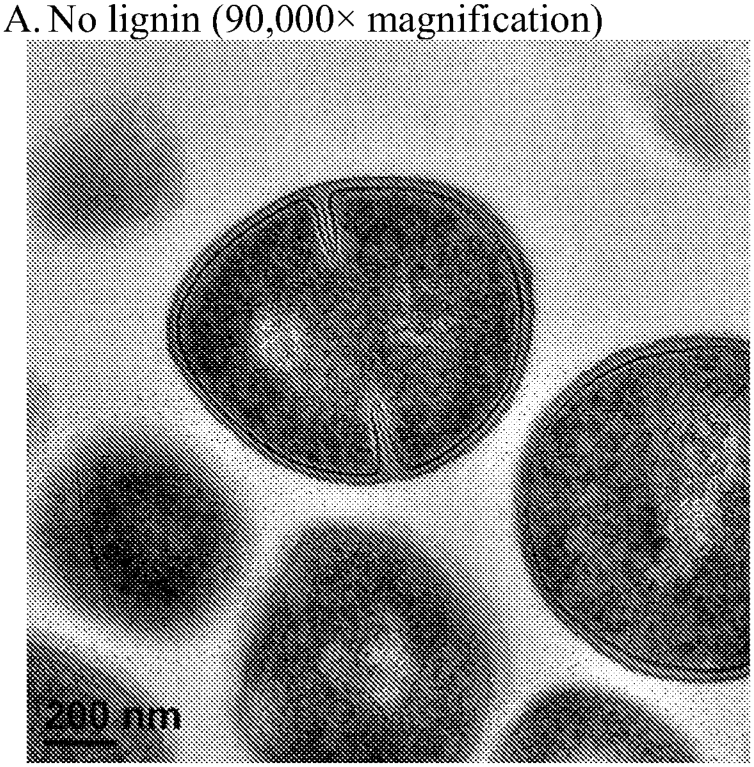
B. 5 mg/mL lignin (90,000×)
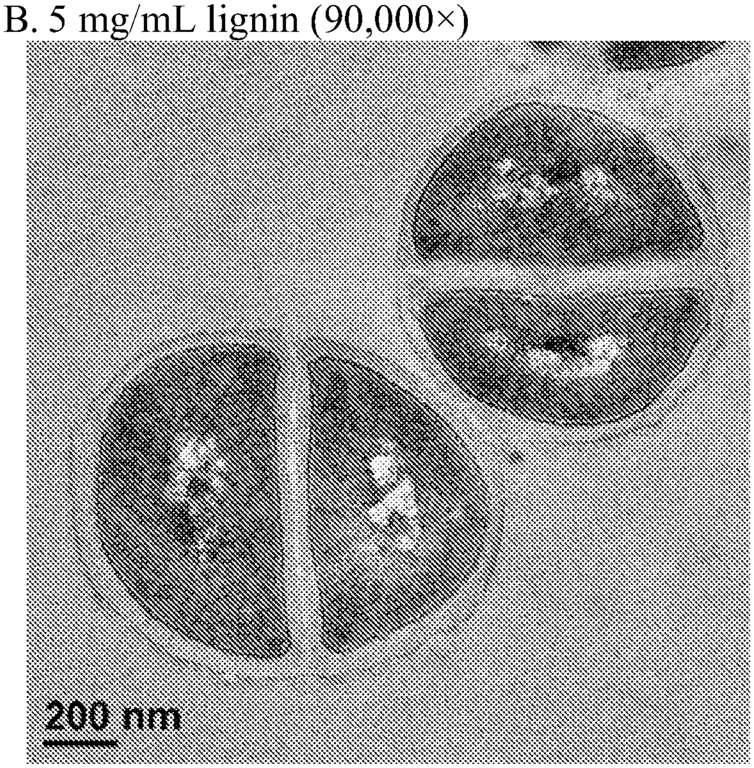
FIG. 21A-B C. No lignin (54,000×)
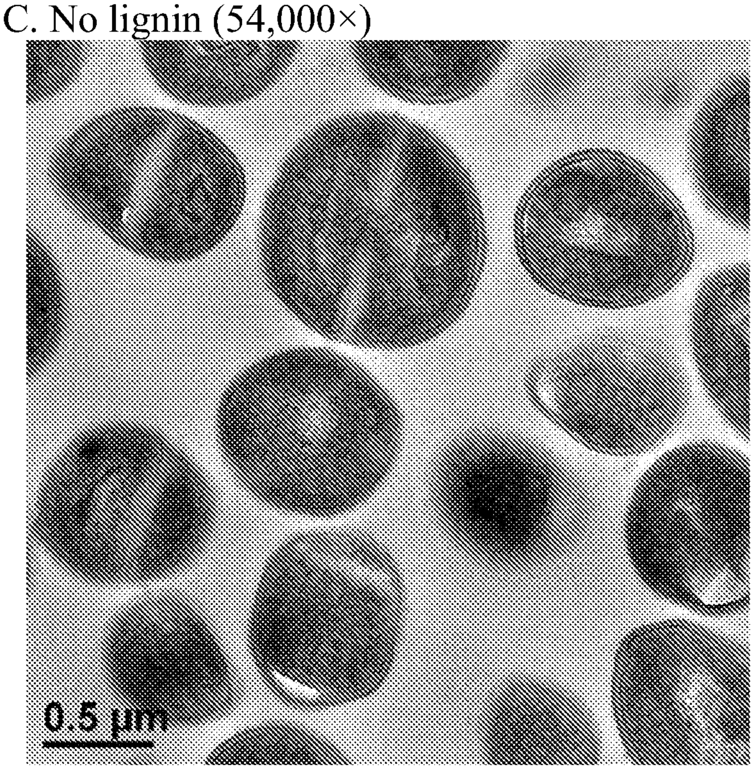
D. 5 mg/mL lignin (54,000×)
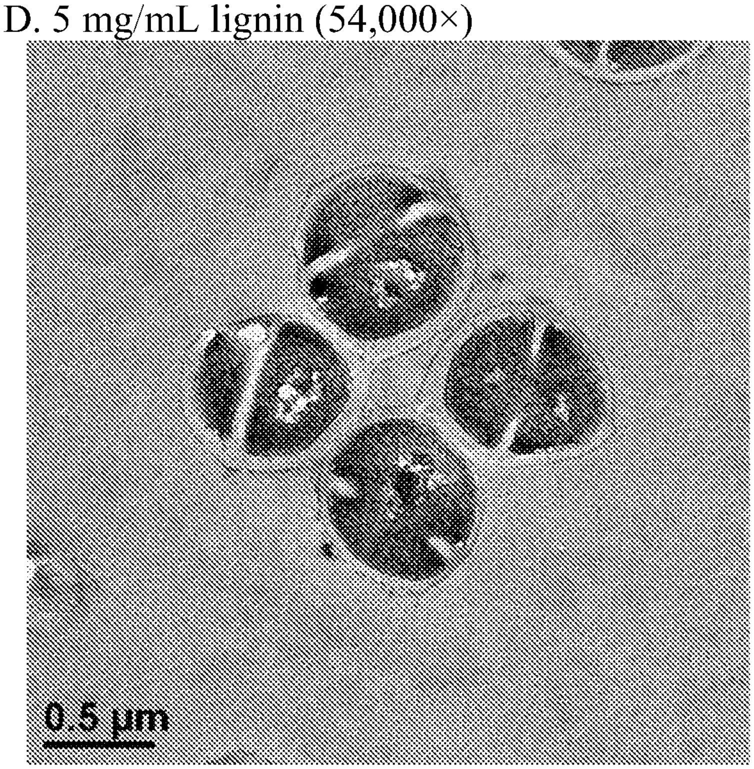
FIG. 21C-D

LIGNIN SOLVATION USING AQUEOUS BIOLOGICALLY COMPATIBLE BUFFERS

CROSS-REFERENCE TO RELATED APPLICATIONS

This application is a U.S. National Stage entry of International Application No. PCT/US2020/013061, filed Jan. 10, 2020, which claims priority to U.S. Provisional Application Ser. No. 62/791,345, filed Jan. 11, 2019 and U.S. Provisional Application Ser. No. 62/815,778, filed Mar. 8, 2019, which are incorporated herein by reference.

BACKGROUND

Lignin is an aromatic polymer present in plant secondary cell walls, where it provides a water-impermeable coating to water-conducting xylem vessels, provides structural support, and acts as a physical barrier against pests and pathogens. Lignin is present in all tracheophytes. The other main constituents of plant cell walls are cellulose and hemicellulosic polysaccharides. Cellulose and lignin are the first and second most abundant biopolymers on Earth, respectively.

Harsh processing conditions including toxic chemicals and high temperature and pressure are used to make plant biomass amenable to enzymatic saccharification of cellulose to generate fermentable sugars. Throughout this process, lignin impedes the access of cellulolytic enzymes to cellulose by physical shielding and serving as a surface onto which the enzymes adsorb irreversibly (Kumar et al. 2012; Li et al. 2013; Lu et al. 2016; Vermaas et al. 2015; and Yang et al. 2016). Therefore, in the context of biomass processing, lignin is perceived as a contaminant that must be removed. Nevertheless, lignin possesses characteristics that make it an ideal substrate for value-added products (Grossman & Vermerris, 2019; Roberto et al., 2016; Schutyser et al., 2018). Accordingly, deriving value-added products from lignin offers an opportunity to offset some costs associated with the production of cellulosic biofuels to make them financially competitive with petroleum-based fuels (Van Rijn et al. 2018).

Lignin's hydrophobicity has prevented comprehensive investigation of its antibacterial activity. The propensity of lignin's aromatic rings to participate in 7-7 stacking (Deng et al. 2012) and for its phenolic hydroxyl and methoxyl groups to undergo intermolecular hydrogen-bonding (Kubo & Kadla, 2005) cause lignin to behave hydrophobically in water, forming largely insoluble aggregates. This property severely limits lignin's utility, when prepared using conventional means, in experiments with aqueous solutions.

Currently, unless lignin is chemically derivatized with anionic moieties, it is typically only solvated by strong bases, organic solvents, ionic liquids (salt in a liquid state), and/or deep eutectic solvents. None of these conditions are compatible with biological or medical applications. To study and/or use lignin-based materials in biomedical applications, it is desirable that the lignin be solubilized in aqueous, biologically compatible media. The solvation of unmodified lignin in aqueous buffers would offer new opportunities for lignin applications while avoiding the cost, labor, and/or toxicity associated with lignin derivatization or organic solvents. Herein we describe aqueous compositions of lignin solvated in biologically compatible Good's buffers.

SUMMARY

Described are aqueous lignin solutions comprising lignin solvated in Good's buffer (GB) solutions. In some embodiments, the aqueous lignin solutions solvated in GB solutions can comprise: (a) lignin extracted with NaOH from the solid biorefinery residues remaining after the liquefaction plus simultaneous saccharification and co-fermentation (L+SScF) of 1% phosphoric acid-pretreated sugarcane bagasse (referred to subsequently as 'sugarcane bagasse lignin' or 'sugarcane lignin' or 'grass lignin') solvated in Good's buffer (GB) solutions, (b) lignin extract with NaOH from sorghum bagasse (referred to subsequently as 'sorghum bagasse lignin' or 'sorghum lignin' or 'grass lignin') solvated in GB solutions, and/or (c) lignin extracted with NaOH from 1% phosphoric acid-pretreated eucalyptus wood chips (referred to subsequently as or 'eucalyptus lignin' or 'hardwood lignin' solvated in GB solutions. Because GB generally have p$K_a$-values in a biologically relevant range, are readily soluble in aqueous solution, and do not tend to influence or participate in biochemical reactions, the described aqueous lignin solutions are readily used in a number of experimental, pharmaceutical, biomedical, and other applications. The described aqueous lignin solutions can contain up to 100 mg/mL or more lignin.

In some embodiments, the GB is zwitterionic. In some embodiments, the GB is an N-substituted aminosulfonic acid. An N-substituted aminosulfonic acid GB can be, but is not limited to 3-morpholinopropane-1-sulfonic acid (MOPS), 4-(2-hydroxyethyl)-1-piperazinepropanesulfonic acid (EPPS), or 3 (cyclohexylamino)-1-propanesulfonic acid (CAPS).

In some embodiments the GB concentration is 0.001 M (1 mM) to 1 M.

In some embodiments, the described aqueous lignin solutions do not contain a chemically derivatized lignin, strong base, organic solvent, ionic liquid, or deep eutectic solvent.

The described aqueous lignin solutions can be diluted in water or aqueous media. An aqueous lignin solution can be filter sterilized. Filter-sterilized aqueous lignin solutions can be used in a variety of biomedical, pharmaceutical and/or therapeutic applications. In some embodiments, an aqueous lignin solution is diluted in water or aqueous media and filter sterilized.

In some embodiments, antimicrobial compositions comprising an aqueous lignin solution are described. The antimicrobial compositions can be, but are not limited to, pharmaceutical compositions. The antimicrobial compositions include antibacterial compositions. In some embodiments, an antimicrobial composition comprises an aqueous lignin solution as described and one or more antibiotics. An antibiotic includes, but is not limited to, a β-lactam (beta-lactam) antibiotic and tunicamycin.

In some embodiments, an aqueous lignin solution can be used as antibacterial treatment. An aqueous lignin solution can be used as an antibacterial treatment in the treatment of Gram-positive bacteria. In some embodiments, the Gram-positive bacterium is *Staphylococcus aureus* (*S. aureus*), *Streptococcus uberis*, or *Streptococcus agalactiae.*

In some embodiments, an aqueous lignin solution can be used as adjuvant to antibiotic therapy such as, but not limited to, β-lactam antibiotic therapy or treatment or tunicamycin therapy or treatment. An aqueous lignin solution can be used as an adjuvant to antibiotic therapy to treat a pathogen such as, but not limited to, a bacterial pathogen. The bacterial pathogen can be a Gram-positive bacterial pathogen. The Gram-positive bacterial pathogen can be, but is not limited to, a *Streptococcus* and a *Staphylococcus*. A *Staphylococcus* can be, but is not limited to, *S. aureus*. A *Streptococcus* can be, but is not limited to, *Streptococcus agalactiae* (*S. agalactiae*) or *Streptococcus uberis* (*S. uberis*). The *S. aureus* can be, but is not limited to, β-lactam-resistant *S. aureus* or β-lactam-susceptible *S. aureus*. In some embodiments, the *S. aureus* can be, but is not limited to, methicillin-resistant *S. aureus* [MRSA] and methicillin-sensitive *S. aureus* [MSSA].

In some embodiments, an aqueous lignin solution can be used as adjuvant to tunicamycin antibiotic therapy or treatment. An aqueous lignin solution can be used as an adjuvant to tunicamycin to treat a pathogen. In some embodiments, the pathogen is a bacterial pathogen. In some embodiments, the pathogen is a fungal pathogen. In some embodiments, the pathogen is a viral pathogen. The bacterial pathogen can be a Gram-positive pathogen. The Gram-positive bacterial pathogen can be, but is not limited to, *Staphylococcus aureus* (*S. aureus*). The *S. aureus* can be, but is not limited to, β-lactam-resistant *S. aureus* or β-lactam-susceptible *S. aureus*, and methicillin-resistant *S. aureus* [MRSA] and methicillin-sensitive *S. aureus* [MSSA].

Tunicamycin is a nucleoside antibiotic that inhibits protein glycosylation. Tunicamycin is active against Gram-positive bacteria, yeasts, fungi and viruses.

In some embodiments, the aqueous lignin solution, alone or in combination with antibiotic therapy can be used to inhibit bacterial growth. Inhibit bacterial growth can comprise slowing bacterial growth rate, preventing bacterial growth, or increasing killing of bacterial cells, as compared to the bacteria in the absence of the aqueous lignin solution. In some embodiments, composition made using the aqueous lignin solution or compositions containing lignin derived from the aqueous lignin solutions have antimicrobial properties.

In some embodiments, the aqueous lignin solution can be used in the manufacture of a composition having antimicrobial properties. In some embodiments, an aqueous lignin solution can be used in the manufacture of functionalized lignin nanoparticles, nanocapsules as delivery vehicles for antibiotics, an antimicrobial salve or cream, and/or lignin-containing polymers impregnated with antibiotics. The antibiotics can be, but are not limited to, β-lactams and tunicamycin.

In some embodiments, an aqueous lignin solution can be used in developing value-added applications of lignin. For example, an aqueous lignin solution can be used in the manufacture of lignin-containing polymers, co-polymers, nanofibers, biomaterials, and nanoparticles, among others. In some embodiments, an aqueous lignin solution can be used in the development or manufacture of thin films, bioplastics and antimicrobial materials. Thin films, bioplastics, and antimicrobial materials can be used, for example, in the manufacture of: protective coatings, antioxidative coatings, coatings on a metallic materials, coatings in food packaging, antioxidative preservatives in food packaging, additives in food packaging films, coatings for food-contacting surfaces, coatings for food preparation surfaces, antimicrobial nanoparticles, and drug delivery nanocapsules, among others. In some embodiments, an aqueous lignin solution can be used in the manufacture of fuel, adhesives, drilling fluids, and dispersants.

In some embodiments, methods preparing aqueous lignin solutions are described. The methods comprise obtaining lignin and combining the lignin with a Good's buffer (GB) in an aqueous solution, thereby solvating the lignin. The lignin is combined with a GB at a concentration of about 0.1 mg/mL to greater than or equal to 100 mg/mL lignin and 0.001 M (1 mM) to 1 M GB. In some embodiments, the lignin is combined with a GB at a concentration of about 0.1 mg/mL to greater than or equal to 100 mg/mL and mixed at 0° C. to 100° C. In some embodiments, lignin is combined with a GB at a concentration of about 0.1 mg/mL to greater than or equal to 100 mg/mL and mixed at 18° C. to 25° C. Using a GB, a ≥100 mg/mL aqueous lignin solution can be prepared in less than 60 minutes, less than 75 minutes, less than 90 minutes, or less than 120 minutes at room temperature. However, lower concentrations of lignin may be used and/or additional time may be used in the preparation.

The source of lignin in the described aqueous lignin solutions and methods of preparing the aqueous lignin solutions is not limited to any particular type of plant lignin. The lignin can be derived from a variety of lignin-containing plants including, but not limited to, angiosperms and gymnosperms. Angiosperms include, but are not limited to, grasses. In some embodiments, the lignin is a grass lignin such as, but not limited to, sorghum lignin, sugar cane lignin, or wheat straw lignin.

The lignin in the described aqueous lignin solutions and methods of preparing the aqueous lignin solutions can be obtained using a variety of processes known in the art. In some embodiments, the lignin is derived from bagasse. In some embodiments, the lignin is a technical lignin (Vishtal et al. BioResources, 2011, 6(3):3547-3568). In some embodiments, the lignin can be from an alkaline extraction process. In some embodiments, the lignin is derived from an industrial lignin-removing process (also termed lignin-extraction process). The industrial lignin-removing process can be, but is not limited to, a kraft process, a sulfite process, an organosolv process, a steam explosion process, a soda process, an autohydrolysis extraction process, an ionic liquid extraction process, or a mechanical milling process. An alkaline extraction process can also be implemented on an industrial scale. In some embodiments, the lignin is obtained from the residues of a lignocellulosic biorefinery. In some embodiments, the lignin is obtained from the solid residues that remain after processing biomass, such as in a biorefinery. In some embodiments, the lignin is obtained from liquefaction plus simultaneous saccharification and co-fermentation of phosphoric acid-pretreated plant material.

In some embodiments, after solvating in a GB, the aqueous lignin solution is diluted. In some embodiments, after solvating in a GB, the aqueous lignin solution is filter sterilized. In some embodiments, after solvating in a GB, the aqueous lignin solution is diluted and filter sterilized. The filter can be, but is not limited to, 0.2 μm filter.

Also described are methods of separating lignin from cellulose or hemicellulose or removing lignin from lignocellulose, using GB. Using GB lowers toxicity of the processes, and may be regenerated. A GB, such as pH-adjusted CAPS, is combined with a lignocellulose composition, such as, but not limited to a bagasse (e.g., lyophilized, shredded sorghum bagasse). After incubation at elevated temperature, the mixture is filtered to separate the filtrate, containing lignin, and insoluble plant material, such as cellulose and hemicellulose. The lignin is precipitated with an anti-solvent, and the anti-solvent may be removed from the GB so that the process may be repeated.

BRIEF DESCRIPTION OF THE FIGURES

FIG. 20A-D. Total ion chromatograms obtained from the pyrolysis of (A) sugarcane bagasse lignin (B) sorghum lignin (C) sorghum bagasse, and (D) the sorghum residues remaining after alkaline extraction of lignin. Peak labels are explained in FIG. 20E.

FIG. 20E. Table identifying peaks in chromatograms of FIG. 20A-D.

FIG. 21A-B. Transmission electron micrographs showing *S. aureus* grown for 2 h in A. 50 mM MOPS and B. 50 mM MOPS+5 mg/mL sugarcane dilute acid lignin (90,000× magnification).

FIG. 21C-D. Transmission electron micrographs showing *S. aureus* grown for 2 h in A. 50 mM MOPS and B. 50 mM MOPS+5 mg/mL sugarcane dilute acid lignin (54,000× magnification).

DETAILED DESCRIPTION

Figure 1:
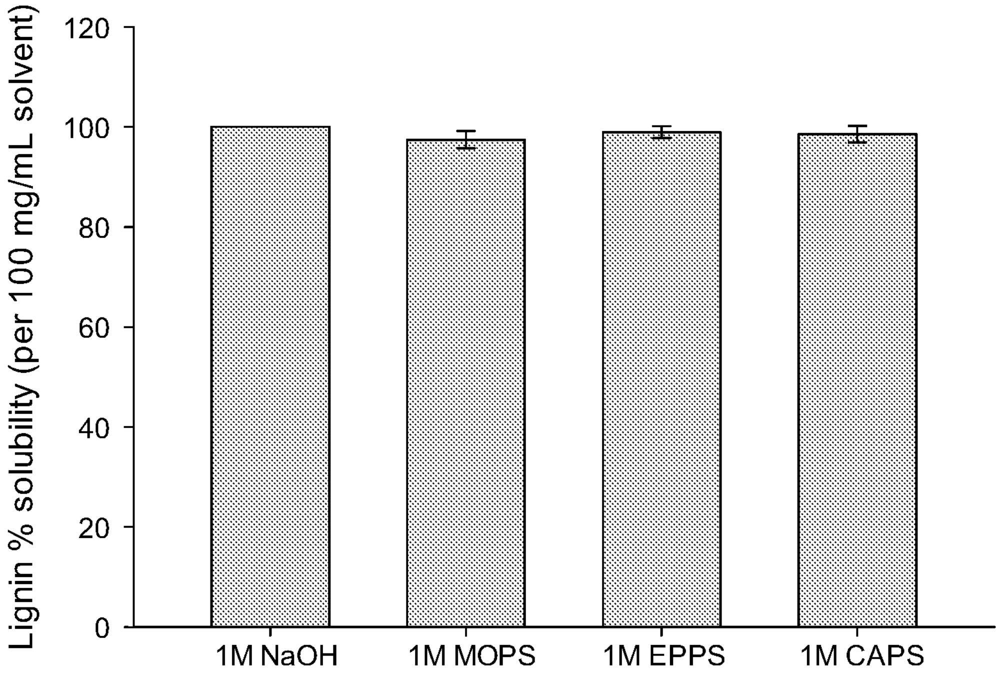
FIG. 1. Graph illustrating the solubility of sugarcane bagasse lignin in 1 M GB. Aqueous lignin solutions of up to or greater than 100 mg/mL were prepared. Each solution was tested separately three times and t-tests were performed between data sets from NaOH (pH 14), MOPS (pH 7.2±0.05), EPPS (pH 8±0.05), and CAPS (pH 10.4±0.05). There was no statistically significant difference in sugarcane lignin solubility between 1 M NaOH and GB (n=3, p≥0.05). Error bars represent sample mean±standard deviation.

Described are lignin solutions comprising lignin solvated in a Good's buffer solution. In some embodiments, the described lignin solvated in a Good's buffer solution comprises: (a) lignin extracted with NaOH from the solid biorefinery residues remaining after the liquefaction plus simultaneous saccharification and co-fermentation (L+SScF) of 1% phosphoric acid-pretreated sugarcane bagasse (referred to subsequently as 'sugarcane bagasse lignin' or 'sugarcane lignin' or 'grass lignin'), (b) lignin extract with NaOH from sorghum bagasse (referred to subsequently as 'sorghum bagasse lignin' or 'sorghum lignin' or 'grass lignin'), and/or (c) lignin extracted with NaOH from 1% phosphoric acid-pretreated eucalyptus wood chips (referred to subsequently as 'eucalyptus lignin' or 'hardwood lignin') solvated in a Good's buffer solution (referred to subsequently as 'aqueous lignin solutions' or 'lignin solutions). The described aqueous lignin solutions offer advantages and improvements over previous lignin solutions in being easier to prepare, lower in toxicity, and more compatible with biological and medical applications.

"Good's buffers" (GB) are a class of non-toxic buffers characterized as hydrogen-bonding zwitterions. GB conform to standards defined by Dr. Norman Good as necessary for the behavior of a biological buffer, including being readily soluble in water, to have minimal salt or ionic influences on water, and to not pass through cell membranes (Good et al., 1966). GB simultaneously possess positively and negatively charged functional groups. The overall charge of a GB is neutral. GB are inherently non-ionic and do not dissociate as salts in solution but instead undergo keto-enol tautomerization (Chruszcz et al. 2005; Laughlin, 1991, Good N E et al. "Hydrogen ion buffers for biological research." Biochemistry 1966, 5:467-477; Ferguson W J et al. "Hydrogen ion buffers for biological research." Anal Biochem 1980, 104:300-310).

Because Good's buffers (GB) generally have $pK_a$-values in a biologically relevant range, are readily soluble in aqueous solution, and do not tend to influence or participate in biochemical reactions, the described aqueous lignin solutions are readily used in a number of experimental, pharmaceutical, biological, and other applications.

In some embodiments, a GB is a zwitterionic N-substituted aminosulfonic acid. In some embodiments a GB contains a negative charge from a sulfonic acid group and a positive charge from a morpholine, piperazine, or cyclohexylamine ring. Suitable GB include, but are not limited to, those listed in Table 1.

TABLE 1

Good's buffers

| Good's buffer | useful pH range |
|---|---|
| 3-morpholinopropane-1-sulfonic acid (MOPS) | 6.5-7.9 |
| 4-(2-hydroxyethyl)-1-piperazinepropanesulfonic acid (EPPS) | 7.3-8.7 |
| 3-(cyclohexylamino)-1-propanesulfonic acid (CAPS) | 9.7-11.1 |
| 2-[4-(2-hydroxyethyl)piperazin-1-yl]sulfonic acid (HEPES) | 6.5-8.2 |
| N-cyclohexyl-2-aminoethanesulfonic acid (CHES) | 9.3-10 |
| 2-(N-morpholino)ethanesulfonic acid (MES) | 5.5-6.7 |
| N-(2-Acetamido)-2-aminoethanesulfonic acid (ACES) | 6.1-7.5 |
| N-(1,1-Dimethyl-2-hydroxyethyl)-3-amino-2-hydroxypropanesulfonic acid (AMPSO) | 8.3-9.7 |
| N,N-Bis(2-hydroxyethyl)-2-aminoethanesulfonic acid (BES) | 6.4-7.8 |
| N-cyclohexyl-3-aminobutanesulfonic acid (CABS) | 10-11.4 |
| N-cyclohexyl-2-hydroxyl3-aminopropanesulfonic acid (CAPSO) | 8.9-10.3 |
| 3-(N,N-bis[2-hydroxyethyl]amino)-2-hydroxypropanesulfonic acid (DIPSO) | 7.0-8.2 |
| N-(2-Hydroxyethyl)piperazine-N'-(4-butanesulfonic acid) (HEPBS) | 7.6-9.0 |
| 3-[4-(2-Hydroxyethyl)-1-piperazinyl]propanesulfonic acid (HEPPS) | 7.3-8.7 |
| 4-(2-Hydroxyethyl)piperazine-1-(2-hydroxypropanesulfonic acid) (HEPPSO) | 7.1-8.7 |
| 4-Morpholinobutanesulfonic acid (MOBS) | 6.5-7.9 |
| β-Hydroxy-4-morpholinepropanesulfonic acid (MOPSO) | 6.2-7.6 |
| 1,4-Piperazinediethanesulfonic acid (PIPES) | 6.1-7.5 |
| Piperazine-N,N'-bis(2-hydroxypropanesulfonic acid) (POPSO) | 7.2-8.5 |
| N-[Tris(hydroxymethyl)methyl]-3-aminobutanesulfonic acid (TABS) | 8.2-9.6 |
| N-[Tris(hydroxymethyl)methyl]-3-aminopropanesulfonic acid (TAPS) | 7.7-9.1 |
| 2-Hydroxy-3-[tris(hydroxymethyl)methylamino]-1-propanesulfonic acid (TAPSO) | 7.0-8.2 |
| 2-[(2-Hydroxy-1,1-bis(hydroxymethyl)ethyl)amino]ethanesulfonic acid (TES) | 6.8-8.2 |
| 2-[(2-amino-2-oxoethyl)-(carboxymethyl)amino]acetic acid (ADA) | 6.0-7.2 |
| 2-amino-2-methyl-1-propanol (AMP) | 9.0-10.5 |
| 2-amino-2-methyl-1,3-propanediol (AMPD) | 7.8-9.7 |

TABLE 1-continued

| Good's buffers | |
|---|---|
| Good's buffer | useful pH range |
| Bicine | 7.6-9.0 |
| Triethanolamine (TEA) | 7.0-8.3 |
| Tris pH | 7.4-8.8 |
| Tris base | 7-9 |
| Bis Tris Propane | 6.3-9.5 |
| Trizma | 7.5-9.0 |

In some embodiments, the GB is 3-morpholinopropane-1-sulfonic acid (MOPS), 4-(2-hydroxyethyl)-1-piperazinepropanesulfonic acid (EPPS), or 3-(cyclohexylamino)-1-propanesulfonic acid (CAPS).

The described aqueous lignin solutions can be in a 0.001 M (1 mM) to 1 M GB solution. In some embodiments, the concentration of GB in the aqueous lignin solution can be about 1 mM, about 2 mM, about 5 mM, about 10 mM, about 25 mM, about 50 mM, about 100 mM, about 200 mM, about 300 mM, about 400 mM, about 500 nmM, about 600 mM, about 700 mM, about 800 mM, about 900 mM, or about 1 M.

The described aqueous lignin solutions can have range of pH-values. In some embodiments, the pH of an aqueous lignin solution can be from about pH 5.5 to about pH 11.5. In some embodiments, the pH of an aqueous lignin solution can be from about pH 6.5 to about pH 11.1. In some embodiments, the pH of an aqueous lignin solution can be from about pH 6.5 to about pH 7.5. In some embodiments, the pH of an aqueous lignin solution can be from about pH 7 to about pH 7.5. In some embodiments, the pH of the aqueous lignin solution is suitable for use with biological research or medical use.

The described aqueous lignin solutions can contain lignin at a concentration of 100 mg/mL or more. In some embodiments, the lignin concentration in a described aqueous lignin solution is ≥20 mg/mL, ≥30 mg/mL, ≥40 mg/mL, ≥50 mg/mL, ≥60 mg/mL, ≥70 mg/mL, ≥80 mg/mL, ≥90 mg/mL, or ≥100 mg/mL.

In some embodiments, the described aqueous lignin solutions do not contain a chemically derivatized lignin, strong base, organic solvent, ionic liquid, or deep eutectic solvent.

"Solvation" is the interaction of a solute (or solute moiety) and the solvent (or co-solvents where GB and water are both co-solvents) which leads to stabilization of the solute species in the solution. Solvation can involve chaotropic de-aggregation, hydrogen bonding, ion-dipole interactions, and/or Van der Waals forces. In the process of solvation, solute is surrounded by a shell of solvent/co-solvent. Lignin is solvated if it forms solvation complexes in the solvent/co-solvent, e.g., Good's buffer.

Methods of Preparing Aqueous Lignin Solutions

Described herein are methods of preparing aqueous lignin solutions. The described methods differ from previously described methods of forming lignin solutions that use ionic liquids and deep eutectic solvents (IL/DES). IL/DES are mixtures containing separate anionic and cationic molecules. In contrast, GB are single, discrete molecules with functional groups possessing a negative and positive charge, thus making them zwitterions. The described methods also differ from previous methods relying on chemical derivatization of the lignin, or the use of strong bases or organic solvents. The described methods comprise obtaining lignin and solvating the lignin in a Good's buffer (GB) solution.

The source of lignin is not limited to any particular type of plant lignin. The lignin can be derived from a variety of plants including, but not limited to, angiosperms and gymnosperms (Campbell & Sederoff, 1996; del Rio et al., 2015; Obst, 1982). In some embodiments, the lignin is a grass lignin such as, but not limited to, sorghum lignin, sugarcane lignin, or wheat straw lignin. In some embodiments, the lignin originates from a woody plant, including, but not limited to, hardwood or softwood species. The hardwood or softwood can be in the form of wood chips. The hardwood or hardwood chips can be, but are not limited to, eucalyptus wood chips and birch wood chips.

"Delignification" is the removal of lignin from lignocellulosic tissue. Delignification can be by mechanical, enzymatic, ionic, and/or thermochemical processes.

"Technical lignin" is the lignin collected after industrial removal from lignocellulosic biomass.

"Anti-solvent" is any agent which precipitates lignin from the GB solution.

A variety of plant processing methods that produce lignin available in the art may be used to obtain the lignin. In some embodiments, the lignin is derived from bagasse. A bagasse is a pulpy fibrous residue left after the extraction of juice from plants. The bagasse can be, but is not limited to, sorghum bagasse and sugarcane bagasse. In some embodiments, the lignin is derived from an industrial lignin-removing process. In some embodiments, the lignin is obtained from a kraft process, sulfite process, organosolv process, steam explosion process, soda process, autohydrolysis extraction process, ionic liquid extraction process, and/or mechanical milling process. In some embodiments, the lignin is obtained from the solid residues that remain after processing biomass, such as in a biorefinery. In some embodiments, the lignin is obtained from the residues produced by a lignocellulosic biorefinery. In some embodiments, the lignin is obtained from liquefaction plus simultaneous saccharification and co-fermentation of phosphoric acid-pretreated plant material. In some embodiments, the lignin is extracted in sodium hydroxide from pretreated or non-pretreated plant bagasse. The sodium hydroxide can be, but it not limited to, 1 M NaOH. In some embodiments, the lignin is obtained from the lignin-rich residue collected after liquefaction plus simultaneous saccharification and co-fermentation (L+SScF) of phosphoric acid-pretreated plant material.

In some embodiments, the lignin is solvated in a GB selected from Table 1. In some embodiments, the GB is zwitterionic N-substituted aminosulfonic acid. In some embodiments, the lignin is solvated in 3-morpholinopropane-1-sulfonic acid (MOPS), 4-(2-hydroxyethyl)-1-piperazinepropanesulfonic acid (EPPS), or 3-(cyclohexylamino)-1-propanesulfonic acid (CAPS).

The lignin can be solvated in 0.001 M (1 mM) to 1 M GB. The GB concentration can be about 1 mM, about 2 mM, about 5 mM, about 10 mM, about 25 mM, about 50 mM, about 100 mM, about 200 mM, about 300 mM, about 400 mM, about 500 mM, about 600 mM, about 700 mM, about 800 mM, about 900 mM, or about 1 M.

The described aqueous lignin solutions can be prepared across a range of pHs. In some embodiments, the lignin is combined with a GB solution at a pH of about pH 5.5 to about pH 11.5. In some embodiments, the lignin is solvated in GB solution at a pH of about pH 6.5 to about pH 11.1. In some embodiments, the lignin is solvated in GB solution at a pH of about pH 6.5 to about pH 7.5. In some embodiments, the lignin is solvated in GB solution at a pH of about pH 7 to about pH 7.5.

The lignin can be combined with a GB solution and solvated at a concentration of about 0.1 mg/mL to greater than or equal to 100 mg/mL lignin. In some embodiments, the lignin is combined with the GB solution and solvated at a concentration of ≥20 mg/mL, ≥30 mg/mL, ≥40 mg/mL, ≥50 mg/mL, ≥60 mg/mL, ≥70 mg/mL, ≥80 mg/mL, ≥90 mg/mL, or ≥100 mg/mL.

The lignin can be combined with a GB solution and solvated at a temperature of 0° C. to 100° C. In some embodiments, the lignin is combined with a GB solution and solvated at 18-25° C. In some embodiments, the lignin is combined with a GB solution and solvated at room temperature. In some embodiments, the lignin is combined with a GB solution and solvated at 18±3° C., 18±2° C., 18±1° C., 18° C., 19±3° C., 19±2° C., 19±1° C., 19° C., 20±3° C., 20±2° C., 20±1° C., 20° C., 21±3° C., 21±2° C., 21±1° C., 21° C., 22±3° C., 22±2° C., 22±1° C., 22° C., 23±3° C., 23±2° C., 23±1° C., 23° C., 24±3° C., 24±2° C., 24±1° C., 24° C., 25±3° C., 25±2° C., 25±1° C., or 25° C.

In some embodiments, the lignin is combined with a 0.001-1 M GB solution at a concentration of about 0.1 mg/mL to greater than or equal to 100 mg/mL. In some embodiments, the lignin is combined with a 0.001-1 M GB solution at a concentration of about 0.1 mg/mL to greater than or equal to 100 mg/mL and mixed at 0° C. to 100° C. In some embodiments, the lignin is combined with a 0.001-1 M GB solution at a concentration of about 0.1 mg/mL to greater than or equal to 100 mg/mL and mixed at 18-25° C.

Using the described methods, ≥100 mg/mL lignin can be solvated in a GB solution in less than 120 minutes at room temperature. In some embodiments, ≥20 mg/mL, ≥30 mg/mL, ≥40 mg/mL, ≥50 mg/mL, ≥60 mg/mL, ≥70 mg/mL, ≥80 mg/mL, ≥90 mg/mL, or ≥100 mg/mL lignin can be solvated in a GB solution in ≤30 min, ≤40 min, ≤50 min, ≤60 min, ≤90 min, or ≤120 minutes at room temperature.

In some embodiments are described methods of precipitating lignin from a Good's buffer solution. The methods can comprise the addition of one or more high-ionic strength ionic salts to a solution of GB-solvated lignin. The GB can be, but is not limited to MOPS, EPPS, and CAPS. The high-ionic strength salt can be, but is not limited to, ammonium sulfate and magnesium chloride.

Precipitation from MOPS, with high-ionic strength ionic salts, suggests that MOPS acts as a chaotropic agent. In the presence of hydrophobic lignin particles, GB may be forced into the hydration shell of lignin where it can form hydrogen bonds with hydroxyl and methoxyl groups and shield aromatic rings from interacting with water so that lignin can de-aggregate and solubilize. With wishing to be bound by theory, it is predicted that GB solvates lignin through two related mechanisms: chaotropic de-aggregation and hydrogen bonding.

Methods of Removing Lignin from Lignocellulose

Also described are methods of separating lignin from cellulose or hemicellulose or removing lignin from lignocellulose, using GB. Using GB lowers toxicity of the process and may be regenerated. A GB, such as CAPS (pH 9.6), is combined with a lignocellulose-containing composition, such as, but not limited to a bagasse (e.g., lyophilized, shredded sorghum bagasse) to form a mixture. The GB can be 0.1-1 M. The GB can be combined with a lignocellulose-containing composition at a ratio of up to 10:1 to 100:1 or greater (mls GB to g bagasse). In some embodiments, the GB is combined with the lignocellulose-containing composition at a ratio 1:1, 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or ≥100:1 (mL GB solution to g bagasse). The mixture is then incubated for sufficient time for the GB to solvate lignin in the lignocellulose-containing composition, e.g., 5 minutes or longer. The mixture can also be incubated at elevated temperature. Incubation of the mixture at elevated temperature can be used to improve efficiency. In some embodiments, the mixture is incubated at 30° C.-100° C. In some embodiments, the mixture is incubated at 30° C., 35° C., 40° C., 45° C., 50° C., 55° C., 60° C., 65° C., 70° C., 75° C., 80° C., 85° C., 90° C., 95° C., or 100° C. Each of the listed temperatures include temperatures within ±3° C., within ±2° C., or within +1° C. After incubation, the mixture is filtered to separate the filtrate, containing lignin, and insoluble plant material, such as cellulose and hemicellulose. The lignin can be precipitated by addition of an anti-solvent, e.g. absolute ethanol. Lignin can be collected by vacuum filtration and/or centrifugation. The anti-solvent can be recovered by application of heat and vacuum, e.g. rotary evaporation. The remaining liquid (GB) can be used to repeat the delignification process.

Methods of Use

The aqueous lignin solutions can be used in the generation of value-added products including polymers, bioplastics and/or their respective subunit residues, films, coatings, antimicrobial nanoparticles, functionalized lignin nanoparticles, drug delivery nanocapsules, delivery vehicles for antibiotics, delivery vehicles for β-lactam antibiotics, delivery vehicles for tunicamycin antibiotics, lignin-containing polymers impregnated with antibiotics, lignin-based bioplastic impregnated with β-lactam antibiotics, lignin-containing polymers impregnated with tunicamycin antibiotics and other biomedical applications. Because of the low toxicity of GB, lignin solvated in GB is attractive for use in biomedical and food-related applications.

The described aqueous lignin solutions can be diluted in water or aqueous media. In some embodiments, a described aqueous lignin solution is filtered. In some embodiments, a described aqueous lignin solution is diluted in water or aqueous media and filtered. Filtering can be performed to remove particles over a certain size, such as, but not limited to, particles greater than 200 nm in size. In some embodiments, a described aqueous lignin solution is filter sterilized. The filter can be, but is not limited to, a 0.2 μm filter. In some embodiments, a described aqueous lignin solution is diluted in water or aqueous media and filter sterilized. Filter-sterilized aqueous lignin solutions can be used in a variety of medical research, pharmaceutical and/or therapeutic applications.

In some embodiments, antimicrobial compositions comprising an aqueous lignin solution are described. An antimicrobial composition can be, but is not limited to, a pharmaceutical composition. In some embodiments, the antimicrobial composition comprises an antibacterial treatment. In some embodiments, an aqueous lignin solution can be used as an antibacterial treatment in the treatment of Gram-positive bacteria. In some embodiments, an aqueous lignin solution can be used as an antibacterial treatment in the treatment of *Streptococcus* and/or *Staphylococcus* infection. In some embodiments, an aqueous lignin solution can be used as an antibacterial treatment in the treatment of *Streptococcus agalactiae, Streptococcus uberis*, and/or *Staphylococcus aureus* infection(s). *Streptococcus* and *Staphylococcus* are Gram-positive bacteria. *S. aureus* is in the phylum Firmicute, class Bacilli, order Bacillales and family Staphylococcaceae. *S. agalactiae* and *S. uberis* are in the phylum Firmicute, class Bacilli, order Lactobacillales, and family Streptococcaceae.

In some embodiments, an aqueous lignin solution can be used as an adjuvant to antibiotic therapy. An "adjuvant" is a pharmacological agent or additive that modifies or enhances the effect of other agents or medical treatments. Adjuvants may be used in combination with an antibiotic to modify or improve the effectiveness of the antibiotic. An antibiotic therapy includes, but is not limited to, β-lactam antibiotic therapy or treatment and tunicamycin antibiotic therapy or treatment.

β-lactams include, but are not limited to: penicillins, penams, penems, cephalosporins, cephamycins, cephems, monobactams, and carbapenems.

Penicillins and penams include, but are not limited to, aminopenicillins, amoxicillin, ampicillin (pivampicillin, hetacillin, bacampicillin, metampicillin, talampicillin) azidocillin, azlocillin, bacampicillin, benzathine benzylpenicillin, benzathine penicillin G, benzylpenicillin (G), benzylpenicillin, carbenicillin, carboxypenicillins, carindacillin, clometocillin, cloxacillin (dicloxacillin, flucloxacillin) dicloxacillin, epicillin, flucloxacillin, hetacillin, ecillinam (pivmecillinam), metampicillin, methicillin mezlocillin, nafcillin, oxacillin, penamecillin penicillin G procaine, penicillin G, penicillin K, penicillin N, penicillin O, penicillin V, pheneticillin, phenoxymethylpenicillin (V), phenoxymethylpenicillin, piperacillin, piperacillin, pivampicillin, procaine benzylpenicillin, propicillin, sulbenicillin, talampicillin, temocillin, ticarcillin, and ureidopenicillins.

Cephalosporins and cephamycins include, but are not limited to, cefacetrile (cephacetrile), cefadroxil (cefadroxyl, duricef), cefalexin (cephalexin, keflex), cefaloglycin (cephaloglycin), cefalonium (cephalonium), cefaloridine (cephaloradine), cefalotin (cephalothin, keflin), cefapirin (cephapirin, cefadryl), cefatrizine, cefazaflur, cefazedone, cefazolin (cephazolin, ancef, kefzol), cefradine (cephradine, velosef), cefroxadine, ceftezole, cefaclor (ceclor, distaclor, keflor, raniclor), cefonicid (monocid), cefprozil (cefproxil, cefzil), cefuroxime (zefu, zinnat, zinacef, ceftin, biofuroksym, xorimax), cefuzonam, cefmetazole, cefotetan, cefoxitin, carbacephems, loracarbef (lorabid), cephamycins, cefbuperazone, cefmetazole (zefazone), cefminox, cefotetan (cefotan), cefoxitin (mefoxin), cefotiam (pansporin), cefcapene, cefdaloxime, cefdinir (sefdin, zinir, omnicef, kefnir), cefditoren, cefetamet, cefixime (fixx, zifi, suprax), cefmenoxime, cefodizime, cefotaxime (claforan), cefovecin (convenia), cefpimizole, cefpodoxime (vantin, pecef, simplicef), ceftеram, ceftamere (enshort), ceftibuten (cedax), ceftiofur (naxcel, excenel), ceftiolene, ceftizoxime (cefizox), ceftriaxone (rocephin), cefoperazone (cefobid), ceftazidime (meezat, fortum, fortaz), oxacephems, latamoxef (moxalactam), cefclidine, cefepime (maxipime), cefluprenam, cefoselis, cefozopran, cefpirome (cefrom), cefquinome, oxacephems, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, and cefuracetime.

Penems include, but are not limited to, faropenem and ritipenem.

Monobactams include, but are not limited to, aztreonam, tigemonam, carumonam, and nocardicin A.

Carbapenems include, but are not limited to, ertapenem, antipseudomonal (doripenem, imipenem, meropenem), biapenem, and panipenem.

In some embodiments, a described aqueous lignin solution can be used as an adjuvant to antibiotic therapy to treat a pathogen. The pathogen can be, but is not limited to, a bacterial pathogen. The bacterial pathogen can be a Gram-positive bacterium. The Gram-positive bacterium can be, but is not limited to, *Staphylococcus* and *Streptococcus*. A *Staphylococcus* can be, but is not limited to *Staphylococcus aureus* (*S. aureus*). *S. aureus* can be, but is not limited to, β-lactam-resistant *S. aureus* or β-lactam-susceptible *S. aureus*. A *Streptococcus* can be, but is not limited to, *S. agalactiae, S. uberis, S. pyogenes, S. dysgalactiae, S. bovis, S. anginosusm, S. sanguinis, S. suis, S. mitis, S. mutans*, and *S. pneumoniae.*

Alone, lignin is known to be modestly inhibitory against *S. aureus*. However, the described aqueous lignin solutions exhibit synergism with antibiotics of the β-lactam family and/or tunicamycin. In *S. aureus* UAMS-1, a methicillin-susceptible (MSSA) clinical isolate with resistance to penicillin and ampicillin, lignin potentiates killing from oxacillin (a methicillin derivative) and restores susceptibility to penicillin and ampicillin. Further, lignin restores oxacillin susceptibility to methicillin-resistant *S. aureus* (MRSA). In some embodiments are described compositions comprising lignin and a β-lactam antibiotic. In some embodiments are described compositions comprising an aqueous lignin solution and a β-lactam antibiotic. In some embodiments are described compositions comprising lignin and tunicamycin. In some embodiments are described compositions comprising an aqueous lignin solution and tunicamycin.

In some embodiments, the aqueous lignin can be used as an adjuvant to antibiotic therapy for use in the dairy industry. In some embodiments, the aqueous lignin can be used as an adjuvant to antibiotic therapy for use in the treatment or prevention of mastitis in dairy animals.

In some embodiments, an aqueous lignin solution can be used in developing value-added applications of lignin. For example, the aqueous lignin solution can be used in the manufacture of lignin-containing polymers and co-polymers, nanofibers, biomaterials, and nanoparticles, among others. In some embodiments, the aqueous lignin solutions can be used in the development or manufacture of thin films, bioplastics and antimicrobial materials. Thin films, bioplastics, and antimicrobial materials can be used, for example, in the manufacture of: protective coatings, antioxidative coatings, coatings on a metallic materials, coatings in food packaging, antioxidative preservatives in food packaging, additives in food packaging films, coatings for food-contacting surfaces, coatings for food preparation surfaces, antimicrobial nanoparticles, and drug delivery nanocapsules, among others. In some embodiments, the aqueous lignin solutions can be used in the manufacture of fuel, adhesives, drilling fluids, and dispersants.

Compared to films and coatings made using lignin dissolved in harsh and/or toxic solvents for synthesis of such products, aqueous lignin solutions are preferred and present fewer obstacles to use with food-, drug-, medical-, and biomedical-related applications.

In some embodiments, a described aqueous lignin solution can be used in the manufacture of antimicrobial materials. In some embodiments, an aqueous lignin solution can be used in the manufacture of functionalized lignin nanoparticles, nanocapsules as delivery vehicles for β-lactam antibiotics and/or tunicamycin, and lignin-based bioplastic impregnated with β-lactam antibiotics and/or tunicamycin.

The described aqueous lignin solutions and methods of making the aqueous lignin solutions can be used to reduce the operating cost gap between petroleum and lignocellulosic refining. In creating value for lignin, the described methods can be used to improve the efficiency and decrease the cost associated with processing of lignin and lignocellulosic biorefining. Lignin solvated in Good's buffer can be used in a variety of applications, including, but not limited to, lignin-containing plastics, polymeric materials, fibers, thermoplastics, polyurethane foams, emulsifier, binders, food additives, dispersant, and ARBOFORM™. The lignin in the described aqueous lignin solutions may also be modified such as, but not limited to, by alkylation, carboxymethylation, or other yet-to-be-discovered derivatization.

The described aqueous lignin solutions may facilitate aqueous covalent crosslinking the lignin with lignin, non-lignin residues, functional groups, monomers, and/or polymers. In some embodiments, the lignin may be derivatized with, or crosslinked to, one or more carboxyl-containing groups. Carboxyl-containing groups include, but are not limited to, carboxylic acid and carboxymethyl groups. In some embodiments, the lignin may be derivatized with, or cross-linked to, one or more amine-containing groups. Lignin may be crosslinked to lignin, non-lignin residues, functional groups, monomers, and/or polymers using a variety of crosslinking agents or methods known in the art. The monomer and/or polymer may be, but is not limited to, vinylamine and/or poly(vinylamine). The crosslinking agent may be, but is not limited to, a carbodiimide compound or, an N-hydroxysuccinimide (NHS) compound. An NHS compound may be, but is not limited to, N-hydroxysulfosuccinimide.

LISTING OF EMBODIMENTS

The subject matter disclosed herein includes, but is not limited to, the following embodiments.

1. An aqueous lignin solution comprising lignin solvated in a Good's buffer solution.

2. The aqueous lignin solution of embodiment 1, wherein a Good's buffer in the Good's buffer solution is a zwitterionic N-substituted aminosulfonic acid.

3. The aqueous lignin solution of embodiment 2, wherein the Good's buffer is selected from the group consisting of: 3-morpholinopropane-1-sulfonic acid (MOPS), 4-(2-hydroxyethyl)-1-piperazinepropanesulfonic acid (EPPS), 3-(cyclohexylamino)-1-propanesulfonic acid (CAPS), 2-[4-(2-hydroxyethyl)piperazin-1-yl]sulfonic acid (HEPES), N-cyclohexyl-2-aminoethanesulfonic acid (CHES), 2-(N-morpholino)ethanesulfonic acid (MES), N-(2-Acetamido)-2-aminoethanesulfonic acid (ACES), N-(1,1-Dimethyl-2-hydroxyethyl)-3-amino-2-hydroxypropanesulfonic acid (AMPSO), N,N-Bis(2-hydroxyethyl)-2-aminoethanesulfonic acid (BES), N-cyclohexyl-3-aminobutanesulfonic acid (CABS), N-cyclohexyl-2-hydroxyl3-aminopropanesulfonic acid (CAPSO), 3-(N,N-Bis[2-hydroxyethyl]amino)-2-hydroxypropanesulfonic acid (DIPSO), N-(2-Hydroxyethyl) piperazine-N'-(4-butanesulfonic acid) (HEPBS), 3-[4-(2-Hydroxyethyl)-1-piperazinyl]propanesulfonic acid (HEPPS), 4-(2-Hydroxyethyl)piperazine-1-(2-hydroxypropanesulfonic acid) (HEPPSO), 4-Morpholinobutanesulfonic acid (MOBS), β-Hydroxy-4-morpholinepropanesulfonic acid (MOPSO), 1,4-Piperazinediethanesulfonic acid (PIPES), Piperazine-N,N'-bis(2-hydroxypropanesulfonic acid) (POPSO), N-[Tris(hydroxymethyl)methyl]-3-aminobutanesulfonic acid (TABS), N-[Tris(hydroxymethyl) methyl]-3-aminopropanesulfonic acid (TAPS), 2-Hydroxy-3-[tris(hydroxymethyl)methylamino]-1-propanesulfonic acid (TAPSO), and 2-[(2-Hydroxy-1,1-bis(hydroxymethyl) ethyl)amino]ethanesulfonic acid (TES).

4. The aqueous lignin solution of embodiment 3, wherein the Good's buffer is selected from the group consisting of MOPS, EPPS, and CAPS.

5. The aqueous lignin solution of any one of embodiments 1-4, wherein the concentration of lignin in the aqueous lignin solution is ≥20 mg/mL, ≥30 mg/mL, ≥40 mg/mL, ≥50 mg/mL, ≥60 mg/mL, ≥70 mg/mL, ≥80 mg/mL, ≥90 mg/mL, or ≥100 mg/mL.

6. The aqueous lignin solution of embodiment 5, wherein the concentration of lignin in the aqueous lignin solution is ≥100 mg/mL.

7. The aqueous lignin solution of any one of embodiments 1-6, wherein the concentration of the Good's buffer in the Good's buffer solution is 1 mM to 1 M.

8. The aqueous lignin solution of embodiment 7, wherein the concentration of the Good's buffer in the Good's buffer solution is 1 M.

9. The aqueous lignin solution of any one of embodiments 1-8, wherein the lignin is a gymnosperm lignin, an angiosperm lignin, or a grass lignin.

10. The aqueous lignin solution of any one of embodiments 1-9, wherein the lignin is derived from an industrial lignin-removing process.

11. The aqueous lignin solution of embodiment 10, wherein the industrial lignin-removing process comprises one or more of: a kraft process, a sulfite process, an organosolv process, a steam explosion process, a soda process, an autohydrolysis extraction process, an ionic liquid extraction process, and a mechanical milling process.

12. A method for preparing an aqueous lignin solution, comprising: (a) obtaining lignin, and (b) combining the lignin with a Good's buffer in an aqueous solution, thereby solvating the lignin.

13. The method of embodiment 12, wherein the obtaining lignin in step (a) comprises isolating lignin from a kraft process, a sulfite process, an organosolv process, a steam explosion process, a soda process, an autohydrolysis extraction process, an ionic liquid extraction process, and/or a mechanical milling process.

14. The method of embodiment 12, wherein the obtaining lignin in step (a) comprises obtaining lignin from residues produced by a lignocellulosic biorefinery.

15. The method of embodiment 12, wherein the obtaining lignin in step (a) comprises liquefaction plus simultaneous saccharification and co-fermentation of phosphoric acid-pretreated plant material.

16. The method of embodiment 12, wherein the obtaining lignin in step (a) comprises extracting lignin from non-pretreated plant biomass with sodium hydroxide, such as 1 M sodium hydroxide.

17. The method of any one of embodiments 12-16, wherein obtaining lignin comprises obtaining lignin from a gymnosperm, an angiosperm dicot, an angiosperm monocot, and/or a plant bagasse.

18. The method of embodiment 17, wherein the grass is sorghum, sugarcane, and/or wheat straw.

19. The method of embodiment 17, wherein the plant bagasse is sorghum bagasse and/or sugarcane bagasse.

20. The method of any one of embodiments 12-19, wherein solvating the lignin in a Good's buffer solution comprising combining the lignin with a Good's buffer solution at 18-25° C.

21. The method of any one of embodiments 12-20, wherein the Good's buffer comprises a zwitterionic N-substituted aminosulfonic acid.

22. The method of embodiment 21, wherein the zwitterionic N-substituted aminosulfonic acid is selected from the group consisting of: 3-morpholinopropane-1-sulfonic acid (MOPS), 4-(2-hydroxyethyl)-1-piperazinepropanesulfonic acid (EPPS), 3-(cyclohexylamino)-1-propanesulfonic acid (CAPS), 2-[4-(2-hydroxyethyl)piperazin-1-yl]sulfonic acid (HEPES), N-cyclohexyl-2-aminoethanesulfonic acid (CHES), 2-(N-morpholino)ethanesulfonic acid (MES), N-(2-Acetamido)-2-aminoethanesulfonic acid (ACES), N-(1,1-Dimethyl-2-hydroxyethyl)-3-amino-2-hydroxypropanesulfonic acid (AMPSO), N,N-Bis(2-hydroxyethyl)-2-aminoethanesulfonic acid (BES), N-cyclohexyl-3-aminobutanesulfonic acid (CABS), N-cyclohexyl-2-hydroxyl3-aminopropanesulfonic acid (CAPSO), 3-(N,N-Bis[2-hydroxyethyl]amino)-2-hydroxypropanesulfonic acid (DIPSO), N-(2-Hydroxyethyl)piperazine-N'-(4-butanesulfonic acid) (HEPBS), 3-[4-(2-Hydroxyethyl)-1-piperazinyl]propanesulfonic acid (HEPPS), 4-(2-Hydroxyethyl)piperazine-1-(2-hydroxypropanesulfonic acid) (HEPPSO), 4-Morpholinobutanesulfonic acid (MOBS), β-Hydroxy-4-morpholinepropanesulfonic acid (MOPSO), 1,4-Piperazinediethanesulfonic acid (PIPES), Piperazine-N,N'-bis(2-hydroxypropanesulfonic acid) (POPSO), N-[Tris (hydroxymethyl)methyl]-3-aminobutanesulfonic acid (TABS), N-[Tris(hydroxymethyl)methyl]-3-aminopropanesulfonic acid (TAPS), 2-Hydroxy-3-[tris(hydroxymethyl) methylamino]-1-propanesulfonic acid (TAPSO), and 2-[(2-Hydroxy-1,1-bis(hydroxymethyl)ethyl)amino] ethanesulfonic acid (TES).

23. The method of any one of embodiments 12-22, wherein the lignin is solvated in the Good's buffer solution at a concentration of ≥20 mg/mL, ≥30 mg/mL, ≥40 mg/mL, ≥50 mg/mL, ≥60 mg/mL, ≥70 mg/mL, ≥80 mg/mL, ≥90 mg/mL, or ≥100 mg/mL.

24. The method of any one of embodiments 12-23, wherein the concentration of a Good's buffer in the Good's buffer solution is 1 mM to 1 M.

25. The method of any one of embodiments 12-24, wherein solvating the lignin in the Good's buffer solution comprises combining the lignin with the Good's buffer solution at 18-25° C.

26. The method of any one of embodiments 12-25, further comprising filter sterilizing the aqueous lignin solution.

27. An antimicrobial composition comprising a lignin solvated in a Good's Buffer solution, such as the aqueous lignin solution of any one of embodiments 1-11.

28. The antimicrobial composition of embodiment 27, further comprising a β-lactam antibiotic.

29. The antimicrobial composition of embodiment 27, further comprising tunicamycin.

30. An aqueous lignin solution for use in treating a microbial infection, the aqueous lignin solution comprising a lignin solvated in a Good's buffer.

31. The aqueous lignin solution of embodiment 30, wherein the aqueous lignin solution further comprises an antibiotic, a β-lactam, and/or a tunicamycin.

32. The aqueous lignin solution of embodiment 30 or 31, wherein the microbial infection comprises a Gram-positive bacterial infection.

33. The aqueous lignin solution of embodiment 32, wherein the Gram-positive bacterial infection comprises a *Staphylococcus, Streptococcus, Staphylococcus aureus, Streptococcus uberis*, and/or *Streptococcus agalactiae* infection.

34. The aqueous lignin solution of embodiment 33, wherein the *Staphylococcus aureus* is β-lactam-resistant *S. aureus*, β-lactam-susceptible *S. aureus*, or a methicillin-resistant *S. aureus.*

35. An aqueous lignin solution for use in inhibiting bacterial growth, the aqueous lignin solution comprising lignin solvated in a Good's buffer, such as the lignin solution of any one of embodiments 1-11.

36. The lignin solution of embodiment 35, wherein the lignin solution further comprises an antibiotic.

37. The aqueous lignin solution of embodiment 36, wherein the antibiotic comprises a β-lactam or a tunicamycin.

38. The aqueous lignin solution of any of embodiments 35-37, wherein the microbial infection comprises a Gram-positive bacterial infection.

39. The aqueous lignin solution of embodiment 38, wherein the microbial infection comprises a *Staphylococcus* or a *Streptococcus* bacterial infection.

40. The aqueous lignin solution of embodiment 38, wherein the Gram-positive bacterial infection comprises a *Staphylococcus aureus, Streptococcus uberis*, or *Streptococcus agalactiae* infection.

41. The aqueous lignin solution of embodiment 40, wherein the *Staphylococcus aureus* is β-lactam-resistant *S. aureus*, a β-lactam-susceptible *S. aureus*, or a methicillin-resistant *S. aureus.*

42. The aqueous lignin solution of any one of embodiments 1-11 for use in inhibiting bacterial growth.

43. The aqueous lignin solution of any one of embodiments 1-11 for use as an adjuvant to antibiotic therapy.

44. A method of precipitating lignin solvated in a GB comprising, adding one or more high-ionic strength ionic salts to a solution of the lignin solvated in a GB.

45. The method of embodiment 44 wherein high-ionic strength salt can be ammonium sulfate or magnesium chloride.

46. A composition comprising lignin wherein the lignin is precipitated from an aqueous lignin solution by addition of one or more high-ionic strength ionic salts to a solution of lignin solvated in GB.

47. An antimicrobial composition manufactured using the aqueous lignin solution of any one of embodiments 1-11.

48. A lignin-containing composition manufactured using the aqueous lignin solution of any one of embodiments 1-11.

49. A method of modifying lignin comprising forming the aqueous lignin solution of any one of embodiments 1-11 and contacting the lignin with one or more chemicals capable of reacting with the lignin.

50. A process of delignifying lignocellulose comprising: adding a Good's buffer to the lignocellulose to form a mixture, incubating the mixture for at least 5 minutes to solvate lignin in the mixture, filtering the mixture to remove solvated lignin from insoluble material, collecting lignin precipitated with an anti-solvent, and removing the anti-solvent to allow repeated delignification.

51. The process of embodiment 50, wherein the Good's buffer is a zwitterionic N-substituted aminosulfonic acid.

52. The process of embodiment 51, wherein the zwitterionic N-substituted aminosulfonic acid is selected from the group consisting of: 3-morpholinopropane-1-sulfonic acid (MOPS), 4-(2-hydroxyethyl)-1-piperazinepropanesulfonic acid (EPPS), 3-(cyclohexylamino)-1-propanesulfonic acid (CAPS), 2-[4-(2-hydroxyethyl)piperazin-1-yl]sulfonic acid (HEPES), N-cyclohexyl-2-aminoethanesulfonic acid (CHES), 2-(N-morpholino)ethanesulfonic acid (MES), N-(2-Acetamido)-2-aminoethanesulfonic acid (ACES), N-(1,1-Dimethyl-2-hydroxyethyl)-3-amino-2-hydroxypropanesulfonic acid (AMPSO), N,N-Bis(2-hydroxyethyl)-2-aminoethanesulfonic acid (BES), N-cyclohexyl-3-aminobutanesulfonic acid (CABS), N-cyclohexyl-2-hydroxyl3-aminopropanesulfonic acid (CAPSO), 3-(N,N-Bis[2-hydroxyethyl]amino)-2-hydroxypropanesulfonic acid (DIPSO), N-(2-Hydroxyethyl)piperazine-N-(4-butanesulfonic acid) (HEPBS), 3-[4-(2-Hydroxyethyl)-1-piperazinyl] propanesulfonic acid (HEPPS), 4-(2-Hydroxyethyl)piperazine-1-(2-hydroxypropanesulfonic acid) (HEPPSO), 4-Morpholinobutanesulfonic acid (MOBS), β-Hydroxy-4-morpholinepropanesulfonic acid (MOPSO), 1,4-Piperazinediethanesulfonic acid (PIPES), Piperazine-N,N'-bis(2-hydroxypropanesulfonic acid) (POPSO), N-[Tris (hydroxymethyl)methyl]-3-aminobutanesulfonic acid (TABS), N-[Tris(hydroxymethyl)methyl]-3-aminopropanesulfonic acid (TAPS), 2-Hydroxy-3-[tris(hydroxymethyl) methylamino]-1-propanesulfonic acid (TAPSO), and 2-[(2-Hydroxy-1,1-bis(hydroxymethyl)ethyl)amino] ethanesulfonic acid (TES).

53. The process of embodiment 52, wherein the Good's buffer is selected from the group consisting of: MOPS, EPPS, and CAPS.

54. The process of any one of embodiments 50-53, wherein the ratio of GB to lignocellulose is 10-100 ml GB to 1 g lignocellulose.

55. The process of any one of embodiments 50-54, wherein the mixture is incubated at 25-100° C.

EXAMPLES

Example 1. Chemical sources. All chemicals, buffers, solutions, and antibiotics were used as received from Sigma-Aldrich or ThermoFisher Scientific. Details on Good's buffers included in Supplemental S1.

Example 2. Lignin sources and preparation. Sugarcane bagasse and/or chipped eucalyptus were pre-treated with 1% phosphoric acid then subjected to liquefaction plus simultaneous saccharification (hydrolysis of polysaccharides to soluble sugars) and co-fermentation (L+SScF) at the University of Florida Stan Mayfield Biorefinery (Perry, FL) (Castro et al., 2014; Geddes et al., 2011; Geddes et al., 2010); solid residues were collected after completion of this process. Sorghum bagasse was obtained after juice extraction. All samples were washed copiously with deionized water in a Buchner funnel lined with filter paper (WHATMAN®) until the flow-through was clear. The samples were then lyophilized for 24-36 hours.

Example 3. Alkaline extraction and purification of lignin. Twenty-five grams lyophilized, ground biomass was added to 500 mL 1 M NaOH in a 1 L Pyrex screw-top bottle with a magnetic stir bar and mixed on a magnetic stirrer, loosely-capped, placed in a water bath set at 80° C. and incubated for 4-6 hours. After incubation at 80° C., the contents were mixed at medium/high speed until cool enough to handle. The liquid was then dispensed evenly into 50 mL Oak Ridge-style tubes (Nalgene) and centrifuged (Beckman-Coulter Avanti® J-26 XP) at 9500 rpm for 15 min. The supernatant was filtered in a Buchner funnel lined with glass GF/A filters (WHATMAN®). The filtrate was poured into a clean Pyrex beaker and, while stirring, was slowly acidified by dropwise addition of 9 M sulfuric acid. Clumps of aggregating lignin transiently appeared around pH 7, and acidification was complete when a viscous, tan-brown suspension formed around pH 3.5. This liquid was dispensed evenly in 50 mL Oak Ridge-style tubes and centrifuged at 9500 rpm for 15 min. The resulting pellet was transferred into a Buchner funnel lined with a 0.45 μm filter (GE MicronSep), and washed with deionized water (1-1.5 L) until the flow-through was clear. The lignin was lyophilized and stored in capped glass vials until further use.

Example 4. Lignin solvation. Lyophilized lignin was solvated at concentrations of 100 mg/mL in 1 M MOPS buffer (pH 7.2±0.05). Lyophilized lignin was also solvated at concentrations of 100 mg/mL in other Good's buffers. Each buffer was prepared at 1 M concentration and pH=p$K_a$. Two-mL Eppendorf tubes were pre-weighed and recorded as "Y". Lignin samples of approximately 100 mg were added to pre-weighed tubes containing one mL buffer. The tubes with buffer and lignin were re-weighed to obtain the actual mass of lignin in each tube (m). Tubes were vortexed, placed on a rocking platform at room temperature for 1-2 hours, then centrifuged at 13,400 rpm for 10 min. The supernatant was removed, and lignin pellets were washed with one mL double-deionized water ($ddH_2O$). After centrifugation (13, 400 rpm for 10 min.), the supernatant was removed, and the pellet was dried for 48-72 hours in open tubes in a 37° C. incubator. Tubes were weighed once lignin pellets were completely dry, and the total mass (tube+pellet) was recorded as "X". The mass of insoluble lignin pellet (Z) was calculated as X−Y, and the lignin solubility (%) as [1−(Z÷m)]×100.

Example 5. Lignin solution preparation. All lignin samples were solvated as described above and diluted for measurement by two methods: "direct solvation" (DS) and "dilute from" (DF). DS samples consisted of lignin solvated in 1 M, 100 mM, 10 mM, and 1 mM buffer and diluted into buffer of the same respective concentration. Prior to measurement, 1 M samples were diluted 50×, 100 mM samples were diluted 20×, and 10 mM and 1 mM samples were measured undiluted. DF samples, including sugarcane bagasse, sorghum, and eucalyptus lignin, were solvated in 1 M buffer then diluted 10×, 100×, and 1000× in HPLC-grade water (Fisher). All DS and DF samples were filtered with a 0.22 μm filter prior to measurements.

Results: Sugarcane, sorghum, and eucalyptus lignin were solvated with three members of the Good's buffer family.

3-morpholinopropane-1-sulfonic acid (MOPS)—pKa=7.2, buffering range 6.5-7.9

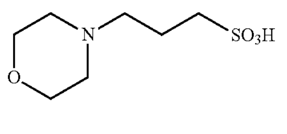 [SMILES: O=S(=O)(O)CCCN1CCOCC1]

4-(2-hydroxyethyl)piperazine-1-propanesulfonic acid (EPPS)—pKa=8.0, buffering range 7.3

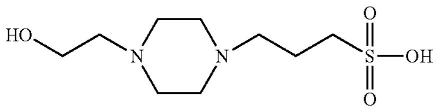 [SMILES: O=S(=O)(O)CCCN1CCN(CCO)CC1]

3-(cyclohexylamino)-1-propanesulfonic acid (CAPS)—pKa=10.4, buffering range 9.7-11.1

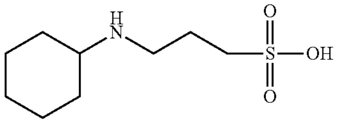 [SMILES: O=S(=O)(O)CCCNC1CCCCC1]

MOPS, EPPS, and CAPS contain a propanesulfonic acid moiety. Any differences in solubility or particle characteristics are predicted to be attributed to influences from the morpholine, piperazine, or cyclohexylamine rings, respectively. There was no statistically significant difference in the solubility of sugarcane bagasse lignin, up to or greater than 100 mg/mL, between 1 M NaOH, MOPS, EPPS, and CAPS (FIG. 1). Accordingly, other GB are expected to solvate lignin similarly. Solubility is shown in Table 2. Lignin from sorghum and sugarcane were equally soluble in all buffers tested. Sugarcane bagasse lignin extracted from solid biorefinery residues was equally solvated by NaOH and Good's Buffers (FIG. 1 and Table 2), and minimally soluble in pure water. While sorghum bagasse lignin was highly soluble in MOPS and EPPS (pH 7.2-8.0±0.05), and thus presumed to be highly soluble in CAPS (pH 10.4±0.05) due to its high pH ($pK_a$), the solubility of eucalyptus lignin seemed to have a greater dependence on the pH ($pK_a$) of the buffer solution (Table 2); the highest solubility of eucalyptus lignin was observed in 1M CAPS buffer, whose pH ($pK_a$) is closest of the three tested buffers to 1M NaOH. The observed variation between hardwood and grass lignin solubility may be due to differences in lignin structure, with hardwood lignins having a higher S:G residue ratio than grass lignins.

TABLE 2

Calculated solubility (%) of sugarcane bagasse, sorghum, and eucalyptus lignins in water, 1M NaOH, and Good's Buffers, values are averages of n ≥ 2 experiments ± standard deviation; n.d. = not done.

| | Sugarcane | Sorghum | Eucalyptus |
|---|---|---|---|
| Water | 1 ± 0.5 | | |
| 1M NaOH (pH 14) | 100 | 100 | 100 |
| 1M MOPS (pH 7.2 ± 0.05) | 97 ± 2 | 99 ± 1 | 34 ± 2 |
| 100 mM MOPS (pH 7.2 ± 0.05) | 24 ± 3 | n.d. | n.d. |
| 10 mM MOPS (pH 7.2 ± 0.05) | 9.5 ± 4.5 | n.d. | n.d. |
| 1 mM MOPS (pH 7.2 ± 0.05) | 3 ± 1 | n.d. | n.d. |
| 1M EPPS (pH 8.0 ± 0.05) | 99 ± 1 | 99 ± 1 | 77 ± 2 |
| 100 mM EPPS (pH 8.0 ± 0.05) | 39 ± 6 | n.d. | n.d. |
| 10 mM EPPS (pH 8.0 ± 0.05) | 5 ± 2 | n.d. | n.d. |
| 1 mM EPPS (pH 8.0 ± 0.05) | 4 ± 1 | n.d. | n.d. |
| 1M CAPS (pH 10.4 ± 0.05) | 99 ± 1 | n.d. | 99 ± 1 |
| 100 mM CAPS (pH 10.4 ± 0.05) | 28 ± 10 | n.d. | n.d. |
| 10 mM CAPS (pH 10.4 ± 0.05) | 6 ± 3 | n.d. | n.d. |
| 1 mM CAPS (pH 10.4 ± 0.05) | 2 ± 1 | n.d. | n.d. |

Example 6. Lignin precipitation. Sugarcane lignin was precipitated from MOPS buffer by adding an equivalent volume of a saturated solution of ammonium sulfate or magnesium chloride. Lignin was precipitated from MOPS with ammonium sulfate and magnesium chloride, indicating that MOPS acts as a chaotropic agent.

Results: Sugarcane bagasse lignin extracted from solid biorefinery residues was equally solvated by NaOH and GB (e.g., MOPS, EPPS, CAPs), and minimally soluble in pure water (FIG. 1 and Table 2). While sorghum bagasse lignin was highly soluble in MOPS and EPPS (pH 7.2-8.0±0.05), and thus presumed to be highly soluble in CAPS (pH 10.4±0.05) due to its high pH ($pK_a$), the solubility of eucalyptus lignin seemed to have a greater dependence on the pH ($pK_a$) of the buffer solution (Table 2); the highest solubility of eucalyptus lignin was observed in 1M CAPS buffer, whose pH ($pK_a$) is closest of the three tested buffers to 1M NaOH. The observed variation between hardwood and grass lignin solubility may be dues to differences in lignin structure, with hardwood lignins having a higher S:G residue ratio than grass lignins.

Example 7. Lignin micellization. Sugarcane lignin micellization was performed in the same manner as solvation with GB, except with 10% and 1% (w/v) Pluronics F-127 and SDS in lieu of buffer. Particle sizes and Zeta potentials of micellar emulsions were then measured undiluted (1×), and at 4× and 10× dilution.

Zeta potential (ζ) and dynamic light scattering (DLS). Particle size and of sugarcane lignin, sorghum lignin, and eucalyptus lignin were measured by DLS and electrophoretic light scattering (ELS), respectively, using Auto Mode on a Malvern Panalytical Zetasizer Ultra (Malvern, UK) with ZS Explorer software, version 1.1.0.656. Triplicate size measurements were made using non-invasive backscatter in a 10×10 $mm^2$ disposable polystyrene cuvette (DTS0012). Triplicate (measurements were made in a folded-capillary cuvette (Malvern DTS1080). A fluorescence filter was applied to all measurements to counter lignin autofluorescence.

Figure 2:
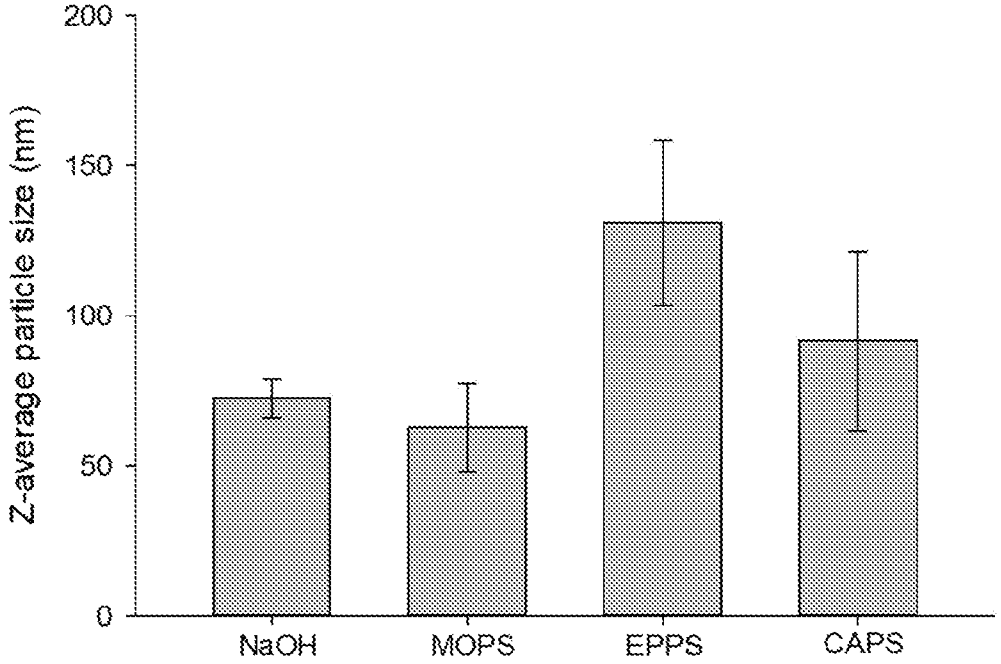
FIG. 2. Graph illustrating Z-average particle sizes of sugarcane bagasse lignin in 1M NaOH, MOPS (pH 7.2±0.05), EPPS (pH 8±0.05), and CAPS (pH 10.4±0.05). Error bars represent the standard deviation. (n≥3 independent experiments).
Figure 3:
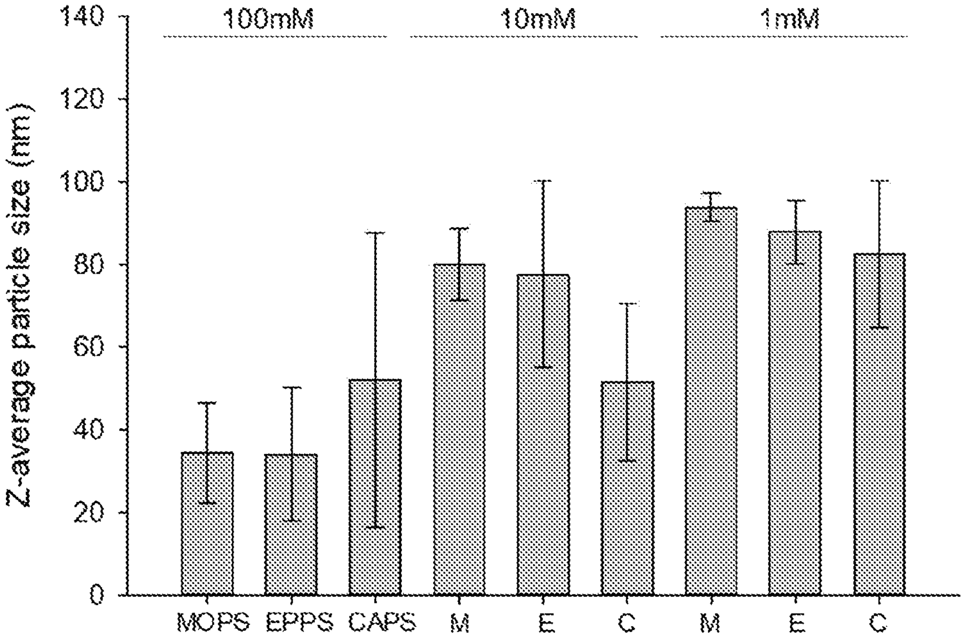
FIG. 3. Graph illustrating Z-average particle sizes of sugarcane bagasse direct solvation (DS)-lignin. Lignin samples directly solvated in 100 mM, 10 mM, and 1 mM MOPS (M) and EPPS (E) displayed Z-averages ≤100 nm. (n≥2). Error bars represent standard deviation.
Figure 4:
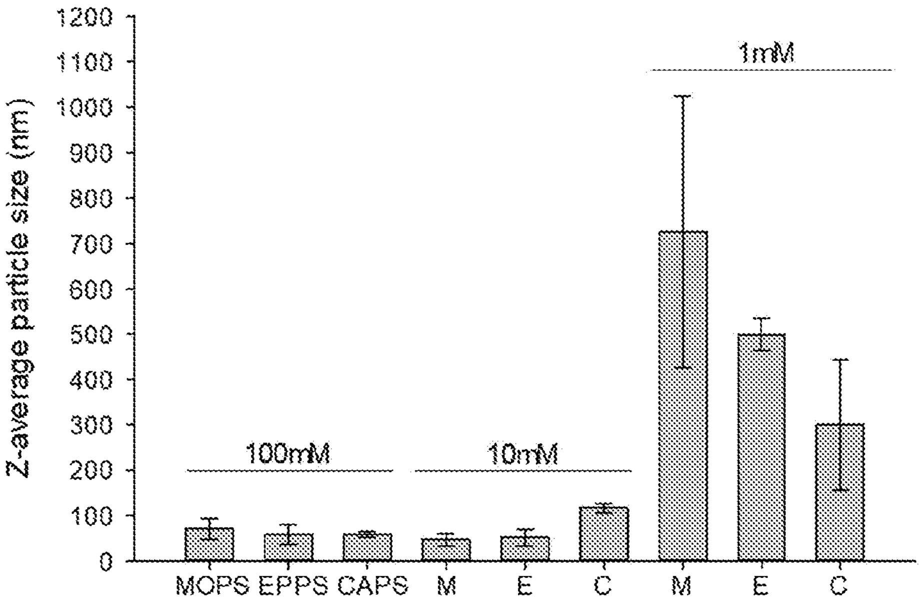
FIG. 4. Graph illustrating Z-average particle sizes of sugarcane bagasse lignin diluted from a concentrated solution (DF-lignin). Lignin samples diluted from 1 M MOPS (M), EPPS (E), and CAPS (C) displayed Z-average particle sizes around 100 nm at concentrations as low as 10 mM. Increased variation in Z-average particle sizes was observed at 1 mM Good's buffer. Error bars represent sample mean±standard deviation (n≥3 independent experiments).

Results: The particle characteristics of sugarcane lignin solvated in Good's buffers or NaOH versus micellized with Pluronics F-127 and SDS were compared. Comparisons between Z-average particle sizes indicated that lignin in 1 M NaOH provided the smallest Z-average particle size. Z-average particle sizes were larger in MOPS, EPPS and CAPS, respectively (see FIG. 2). Lignin solvated in NaOH and MOPS had Z-averages below 100 nm (FIG. 2). However, analyses of DS- and DF-lignin samples at 100 mM, 10 mM, and 1 mM concentrations indicate that particle sizes from lignin solvated in MOPS, EPPS, and CAPS are routinely around 100 nM at buffer concentrations as low as 10 mM (FIG. 3 and FIG. 4). At 1 mM, DF-lignin in GB (e.g., MOPS, EPPS, CAPs) displayed particle sizes larger than 200 nm (FIG. 4). Such particles are predicted to occur only if the particles underwent re-aggregation after filtration, since all samples passed through a 0.2-μm filter after dilution and prior to measurement. This observation suggests an inflection point of Good's Buffer solvation capability exists at concentrations <10 mM. Measurements taken with vertically polarized filters agreed with data from measurements obtained with the fluorescent filter. Both methods essentially measured the largest dimension of the particle, which is typically 100 nm or less. The measurements obtained from the addition of a horizontally polarized filter indicated the lignin particles had a vertical:horizontal (height:width) ratio of approximately 5:1, indicating the formation of a hydration shell with an ellipsoidal shape, rather than a spherical shape. Since the GB we tested all contained propanesulfonic acid moieties and differed only in their N-substituted rings, the differences between particle size and shape can be attributed to non-ionic interactions between lignin, water, and the N-substituted rings of GB.

Figure 5:
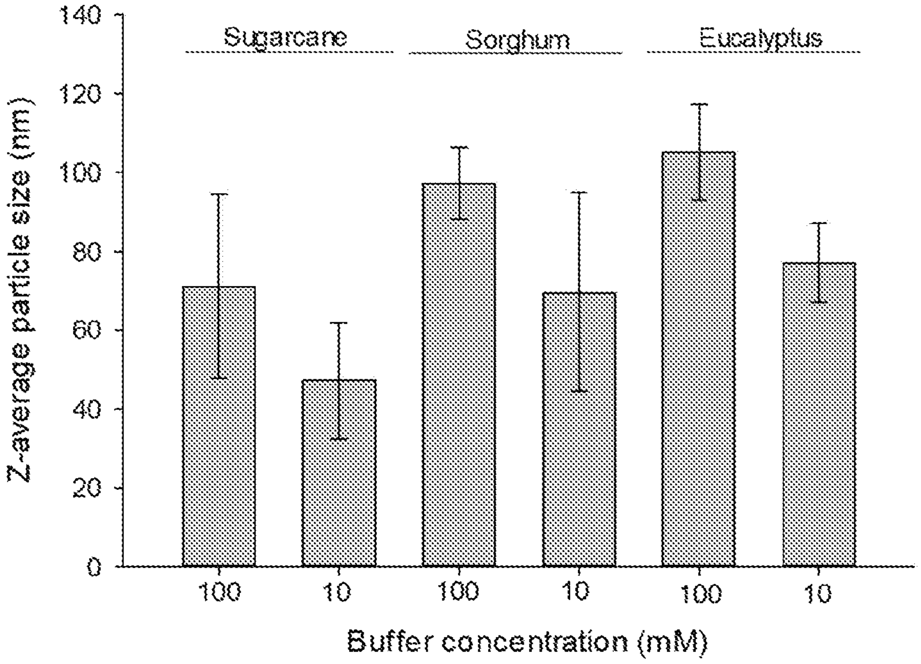
FIG. 5. Graph illustrating MOPS-solvated sugarcane, sorghum, and eucalyptus DF-lignin Z-average particle sizes. Grass and hardwood lignins display particle sizes around 100 nm at MOPS concentrations as low as 10 mM, consistent with results from sugarcane DS- and DF-lignin samples. Error bars represent the standard deviation (n≥2 independent experiments).

The similarities in particle sizes between NaOH and GB indicate GB act as non-ionizing solvents of lignin, at buffer concentrations of 10-1000 mM. Comparison of DF-lignin Z-averages of sorghum and eucalyptus lignin in MOPS compared with sugarcane lignin indicated Z-averages for all MOPS-solvated lignin samples are about 87±20 nm (FIG. 5). The data indicate that lignin from a variety of sources can be solvated in GB. The solvated lignins have similar particle characteristics in GB.

Figure 6:
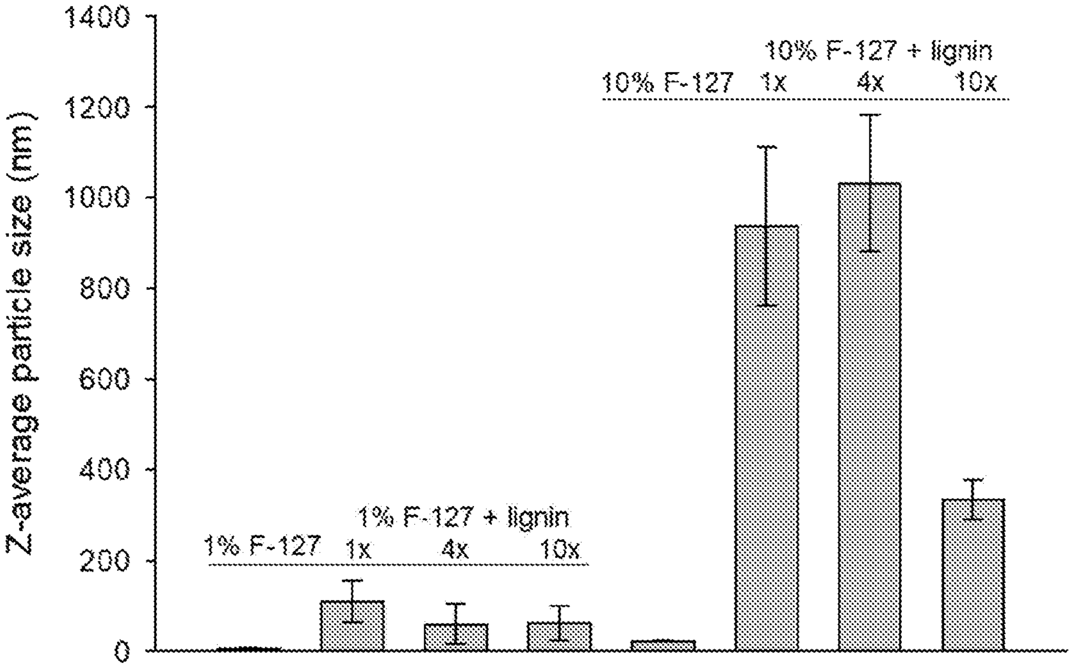
FIG. 6. Graph illustrating Z-average particle sizes of Pluronics F-127 (F-127) micelles with and without sugarcane lignin. F-127 at concentrations of 1% and 10% (w/v), both of which are above the CMC, formed micelles in the presence and absence of lignin. Lignin-containing micelles were measured undiluted (1×) and diluted 4× and 10×. Error bars represent the standard deviation (n≥2 independent experiments).
Figure 7:
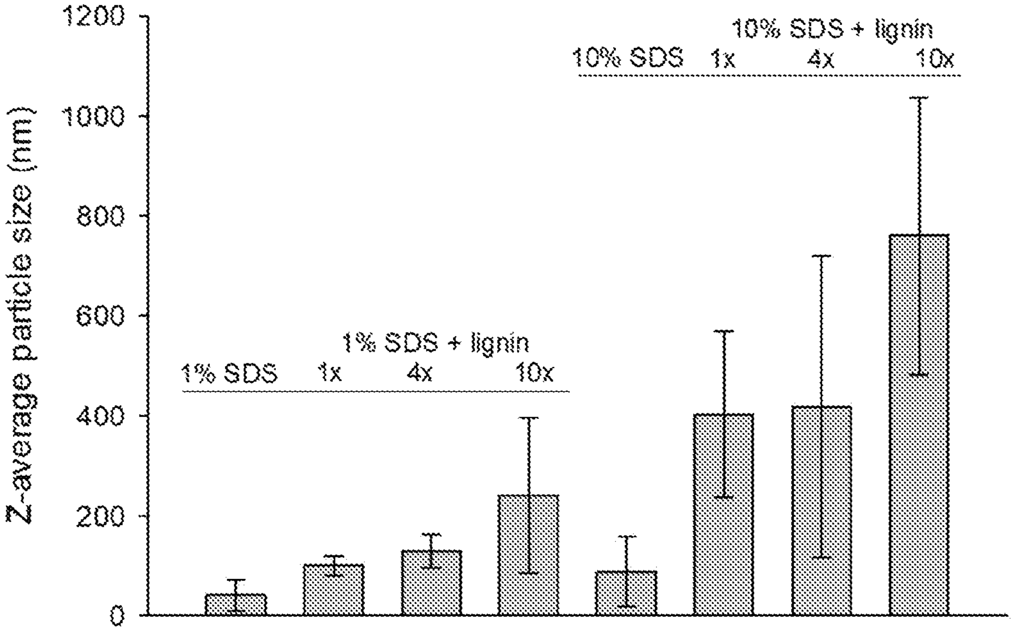
FIG. 7. Graph illustrating Z-average particle sizes of sodium dodecyl sulfate (SDS) micelles with and without sugarcane lignin. SDS at concentrations of 1% and 10% (w/v), both of which are above the CMC, formed micelles in the presence and absence of lignin. Lignin-containing micelles were measured undiluted (1×) and diluted 4× and 10×. Error bars represent the standard deviation (n≥2 independent experiments).

In order to differentiate between lignin solvation and lignin micellization, micelles of Pluronics F-127 and SDS were formed in the presence and absence of sugarcane lignin. The limited solubility of lignin in micellization with F-127 and SDS was apparent from the mass of the insoluble lignin pellets that remained, which in some cases was greater than the original mass of lignin added (Table 3). While some lignin was taken up into micelles as indicated by the increased size of SDS and F-127 micelles with lignin (FIG. 6-7), the increased mass of the insoluble pellet was likely caused by lignin becoming coated with F-127 and SDS during the procedure in a way that prevented removal during subsequent washing steps. F-127 is a tri-block co-polymer consisting of two poly(ethylene glycol) (PEG) blocks flanking a central poly(propylene glycol) block; PEG and ethylene glycol have been well-characterized as forming hydrogen bonds with lignin (Kadla et al. Macromolecules. 2003; 36(20):7803-11; Mu et al. ACS Sustain Chem Eng. 2016; 4(3):1840-9; Jin et al. Bioresour Technol. 2011; 102(3): 3581-3). SDS binds with polymers through electrostatic and hydrophobic interactions and because of its lipid-like structure would not be expected to become unbound by water. Altogether, these are the most likely explanations for the increased mass of insoluble pellets from lignin micellization. The data suggest the lignin is not solvated by micellization.

Figure 8:
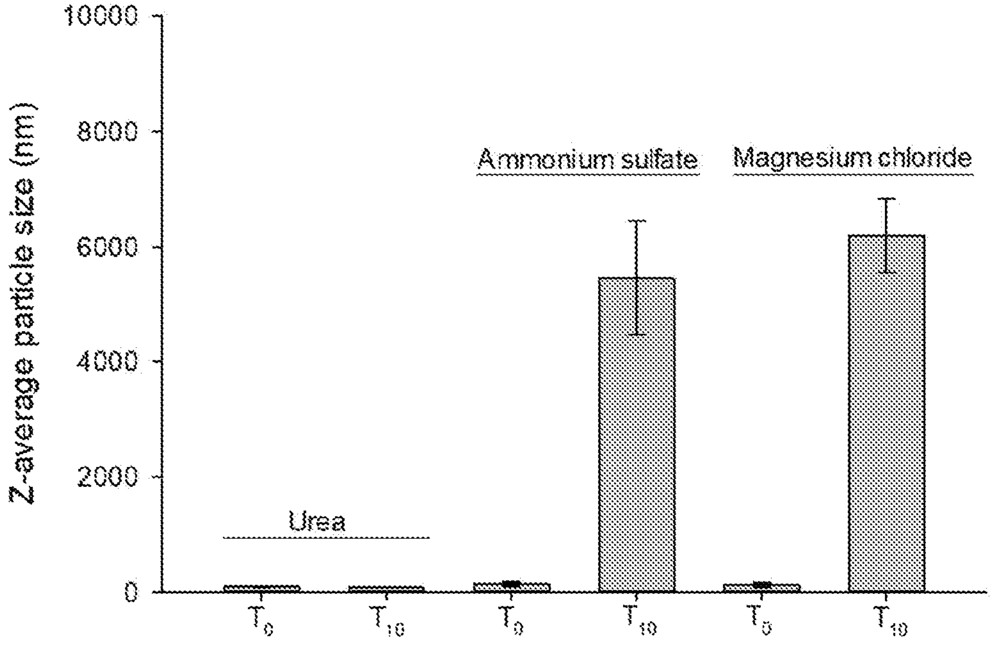
FIG. 8. Graph illustrating Z-average particle sizes of MOPS-solvated sugarcane lignin following the addition of chaotropic and kosmotropic solutes. Particle size measurements taken immediately prior to (To) and up to 10 minutes after ($T_{10}$) addition of saturated urea demonstrate no change in particle size, while saturated ammonium sulfate and magnesium chloride solutions caused the Z-average particle size to increase indicating particle aggregation and precipitation. Error bars represent the standard deviation (n≥2 independent experiments).

Sugarcane lignin solvated in MOPS was precipitated with magnesium chloride and ammonium sulfate. Baseline measurements of particle size were measured prior to addition of salts ($T_0$), after which the salt solutions were added, and measurements were taken for up to 10 minutes ($T_{10}$). The 5-10-fold increase in particle size following salt addition indicated precipitation of lignin (FIG. 8).

Figure 9:
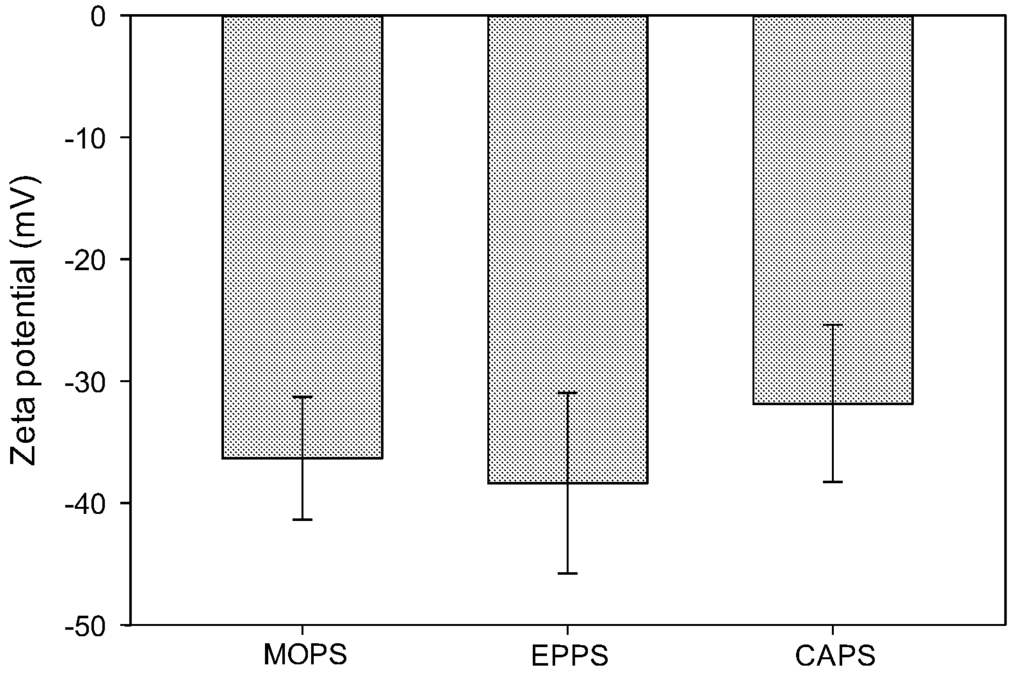
FIG. 9. Graph illustrating zeta potential values of sugarcane lignin in 1 M MOPS, EPPS, and CAPS. The electronegativity of sugarcane lignin particles (<−30 mV) indicates high colloidal stability in GB solutions. Error bars represent the standard deviation (n≥4 independent experiments).

Zeta potential values were measured for sugarcane lignin solvated in MOPS, EPPS, and CAPS. A Student's t-test indicated there is no significant difference in zeta (ζ) potential values between lignin solvated in MOPS and EPPS and between lignin solvated in MOPS and CAPS (n≥12, p≥0.05). However, there was a significant difference between the ζ potential values for lignin solvated in EPPS and lignin solvated in CAPS (n=12, p=0.0306) (FIG. 9). Overall, the ζ potential values for sugarcane lignin solvated in MOPS, EPPS, and CAPS having distinct structures indicates GB provide stable lignin solutions.

Figure 10:
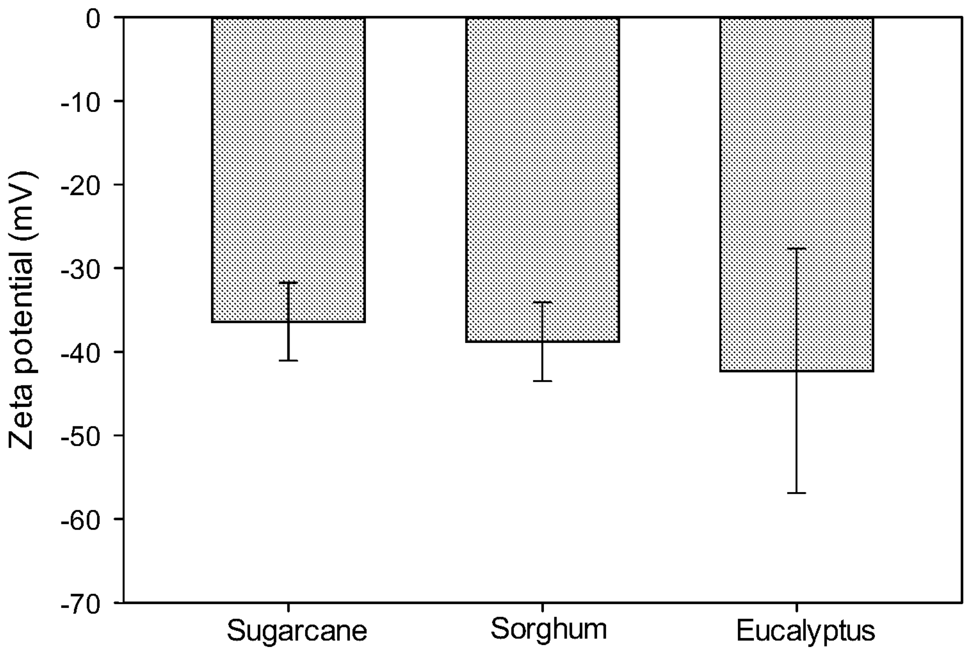
FIG. 10. Graph illustrating zeta potential comparisons between grass and hardwood lignins in MOPS. Lignins solvated in MOPS display consistent (values between which there were no statistically significant differences (n 9, p 0.1). Error bars represent sample mean±standard deviation.

The data in FIG. 10 indicate that lignin from both grass and hardwood can be solvated in MOPS to provide equally stable lignin solutions.

Example 8. Particle size and stability (Zeta potential). To determine if the particle size and stability was influenced by the concentration of Good's buffer in which lignin was solvated, or by the act of diluting a concentrated lignin solution into water, lignin samples were solvated and prepared for measurement by two methods: "direct solvation" (DS) and "dilute from" (DF). DS samples consisted of lignin solvated in 1 M, 100 mM, 10 mM, and 1 mM Good's buffer and diluted into buffer of the same respective concentration. Prior to measurement, 1 M samples were diluted 50×, 100 mM samples were diluted 20×, and 10 mM and 1 mM samples were measured undiluted. DF samples were solvated in 1 M buffer then diluted 10×, 100×, and 1,000× in HPLC-grade water. Like DS samples, 1 M DF samples were diluted 50× prior to measurement, while all other DF samples were measured undiluted. All DS and DF samples were filtered through a 0.22-μm polyvinylidene difluoride (PVDF; Genesee Scientific, San Diego, CA) filter prior to measurements. Particle size and (were measured by dynamic

TABLE 3

Solubility and stability of sugarcane lignin in micelle-forming solutions, values are averages of n ≥ 2 experiments ± standard deviation.

| Solution | m (mg) | Y (empty tube mass) | X (tube + pellet mass) | Z (insoluble pellet mass) | Calculated solubility (%) | ζ potential (mV) |
|---|---|---|---|---|---|---|
| 10% F-127 | 118 ± 29 | 1041 ± 3 | 1168 ± 30 | 127 ± 28 | Negligible | −3 ± 2 |
| 1% F-127 | 104 ± 1 | 1043 ± 3 | 1152 ± 6 | 109 ± 3 | Negligible | −13 ± 6 |
| 10% SDS | 103 ± 2 | 1041 ± 3 | 1125 ± 2 | 83.5 ± 1 | 19 ± 1 | −38 ± 4 |
| 1% SDS | 98.7 ± 9 | 1040 ± 5 | 1142 ± 6 | 102 ± 7 | Negligible | −39 ± 4 |

The effects of chaotropic and kosmotropic co-solutes was demonstrated by adding an equivalent volume (1 mL) of saturated ammonium sulfate, magnesium chloride, or urea to 1 mL of 100 mM direct solvation (DS)-lignin. To confirm the chaotropic activity of MOPS, we predicted that the addition of another chaotrope, urea, to a solution of MOPS-solvated lignin would not have a precipitative effect on lignin, while the addition of kosmotropic salts magnesium chloride and ammonium sulfate would cause precipitation. These predictions were confirmed as shown by the substantial increase in particle sizes after the addition of kosmotropic salts, but not after the addition of urea (FIG. 8), despite an increase in the overall solute concentration.

(DLS) and electrophoretic light scattering (ELS), respectively, using Auto Mode on a Malvern Panalytical Zetasizer Ultra (ZSU; Malvern, UK) with ZS Explorer software, version 1.1.0.656. Triplicate size measurements were made using non-invasive backscatter in a 10×10 $mm^2$ disposable polystyrene cuvette (Malvern DTS0012). Triplicate (measurements were made in a folded-capillary cuvette (Malvern DTS1080). A fluorescence filter (proprietary to the instrument) was applied to counter lignin autofluorescence. Measurement of particles with vertically and horizontally polarized filters provided the general equivalents of particle height and width, respectively.

Example 9. β-lactam disk diffusion susceptibility test. *S. aureus* is well-known to possess and easily gain resistance to antibiotics, particularly to β-lactam antibiotics such as penicillin and methicillin (Chambers and Deleo, Nat Rev Microbiol. 2009; 7:(629-641)). Methicillin-susceptible and methicillin-resistant *S. aureus*, UAMS-1 and LAC-13C, respectively, were streaked for isolation on tryptic soy agar (TSA) plates and incubated for 24 hours at 37° C. Overnight cultures were prepared by picking a single colony of each strain from its plate and adding to separate 3 mL sterile tryptic soy broth (TSB) in a 5 mL culture tube and incubating 14-16 h at 37° C. and 250 rpm. Next, the optical density at 600 nm ($OD_{600}$) was measured to prepare fresh 50 mL cultures with $OD_{600}$=0.1 to be grown for 2-3 hours at 37° C. and 250 rpm. Cultures were pelleted by centrifugation at 4500 rpm, then resuspended and concentrated in 500 μL sterile 1× Hank's Balanced Salt Solution (HBSS). An aliquot of 250 μL from each culture was pipetted onto 1) a TSA plate containing 50 mM MOPS and 2) a TSA plate containing 50 mM MOPS and 5 mg/mL lignin. To achieve lawn-style growth, cells were spread across the plates with sterile glass beads. Finally, paper disks containing 0.2 μg (UAMS-1) or 1 μg (LAC-13C) oxacillin, 2 μg (UAMS-1) or 10 μg (LAC-13C) ampicillin, and 2 μg (UAMS-1) or 10 μg (LAC-13C) penicillin were placed on the agar, then the plates were incubated for 24 h at 37° C. and visually inspected for zones of clearance (no growth) around the disks indicating susceptibility to the specific antibiotic.

Statistical analysis: All graphs, descriptive statistics, and t-tests were generated with SigmaPlot 14.

Figure 11:
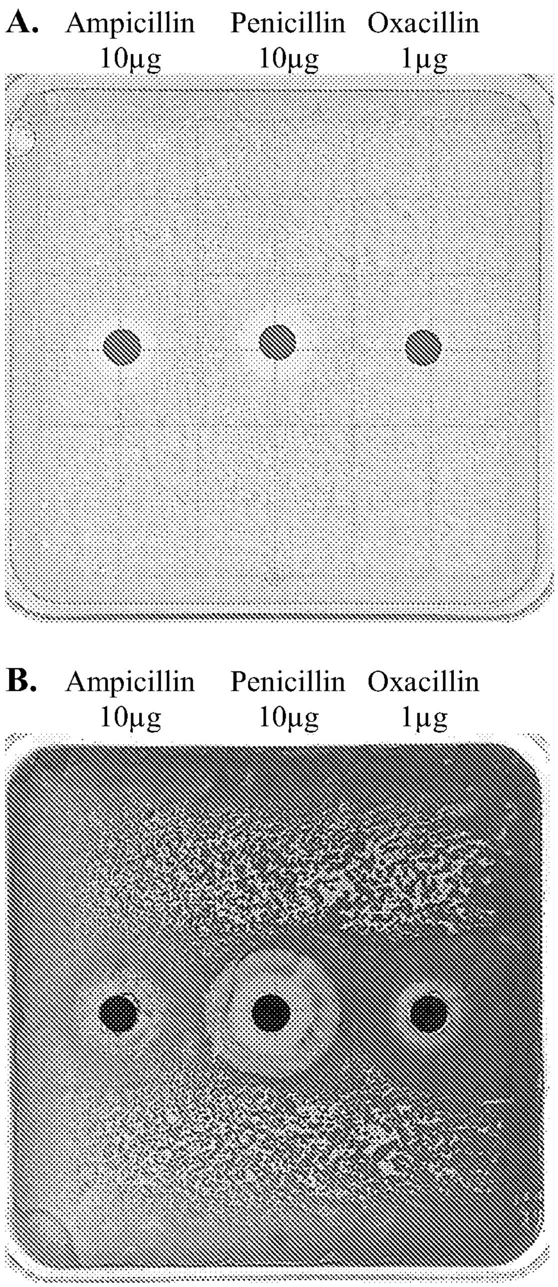
FIG. 11. *S. aureus* LAC-13C β-lactam disk diffusion susceptibility test. A. (top) In tryptic soy agar (TSA) without lignin, *S. aureus* LAC-13C (a methicillin-resistant [MRSA] *S. aureus* strain) is resistant to oxacillin, a methicillin derivative. B. (bottom) In the presence of 5 mg/mL lignin, MRSA exhibited increased sensitivity/susceptibility to oxacillin.
Figure 12:
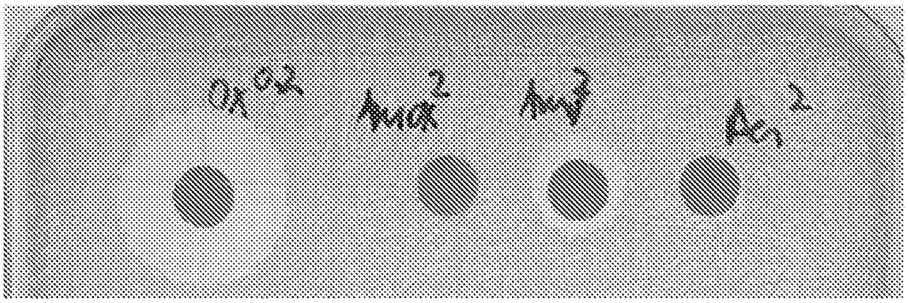
FIG. 12. *S. aureus* UAMS-1 β-lactam disk diffusion susceptibility test. A. (top) In TSA without lignin, *S. aureus* UAMS-1 (a methicillin-sensitive *S. aureus* [MSSA] strain) is moderately resistant to ampicillin and penicillin, but sensitive/susceptible to oxacillin. B. (bottom) In the presence of 5 mg/mL lignin, *S. aureus* UAMS-1 exhibited increased sensitivity/susceptibility to ampicillin, penicillin, and oxacillin.
Figure 12:
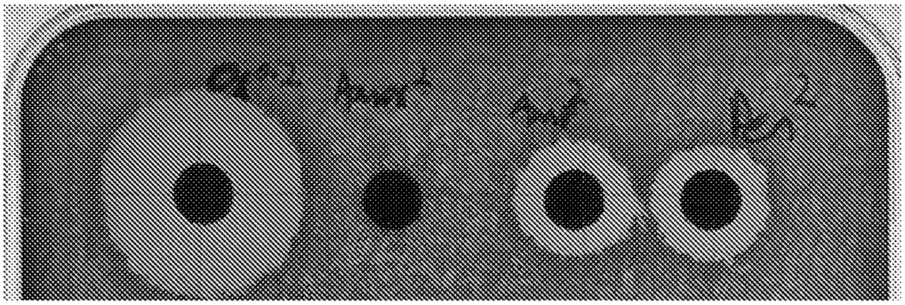

Results: A β-lactam disk diffusion susceptibility test was designed to determine antibiotic sensitivity/susceptibility of bacteria to these antibiotics in the presence and absence of MOPS-solvated lignin. These assays provided evidence of lignin's ability to increase susceptibility to β-lactams in methicillin-resistant and methicillin-susceptible strains of *S. aureus*. The results demonstrated that lignin increased sensitivity/susceptibility to β-lactams in both MRSA LAC-13C and MSSA UAMS-1 to ampicillin, penicillin, and oxacillin (FIG. 11 and FIG. 12). *S. aureus* LAC-13C was completely resistant to oxacillin in the absence of lignin, but sensitive to oxacillin in the presence of lignin (FIG. 11). *S. aureus* UAMS-1 was completely or nearly completely resistant to ampicillin and penicillin in the absence of lignin, but at least partially sensitive/susceptible to ampicillin and penicillin in the presence of lignin (FIG. 12). Lignin also increased sensitivity of *S. aureus* UAMS-1 to oxacillin (FIG. 12). These results indicate that solubilized lignin can be used as an adjuvant to antibiotic therapy.

Example 10. Solvation of lignin in GB. Using the methods described above lignin was solvated in 3-morpholinopropane-1-sulfonic acid (MOPS), 4-(2-hydroxyethyl)-1-piperazinepropanesulfonic acid (EPPS), 3 (cyclohexylamino)-1-propanesulfonic acid (CAPS), 2-[4-(2-hydroxyethyl) piperazin-1-yl]sulfonic acid (HEPES), N-cyclohexyl-2-aminoethanesulfonic acid (CHES), and 2-(N-morpholino) ethanesulfonic acid (MES). Lignin was similarly solvated in each of these buffers.

Figure 13:
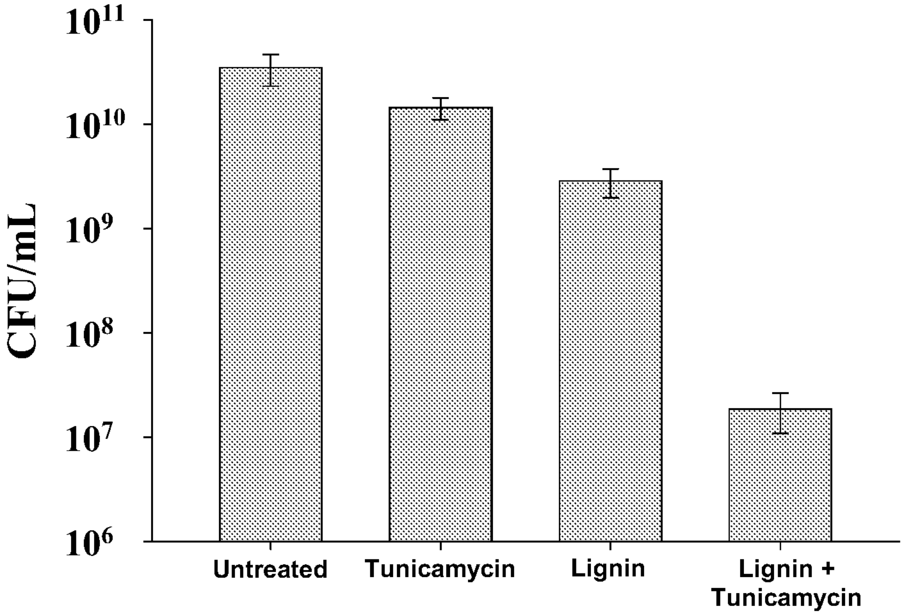
FIG. 13. Graph illustrating inhibition of *S. aureus* UAMS-1 growth in the presence of sub-minimal inhibitory concentration (sub-MIC) tunicamycin (added at time of bacterial inoculation), MOPS-solvated lignin, and the combination of sub-MIC tunicamycin and MOPS-solvated lignin. Data represent the average of n=3 biological replicates, error bars represent SEM. *p=0.05, **p<0.001.

Example 11. Tunicamycin susceptibility. *S. aureus* UAMS-1 liquid cultures were grown for 24 hours in TSB alone (untreated), TSB supplemented with 2 μg/ml tunicamycin (sub-minimal inhibitory concentration; sub-MIC), TSB supplemented with 5 mg/ml MOPS-solvated lignin, or TSB supplemented with 2 μg/ml tunicamycin (sub-MIC) and 5 mg/ml MOPS-solvated lignin. Viability of each culture after 24 hours was measured by colony forming units (CFU) enumeration. 5 mg/ml MOPS-solvated lignin alone inhibited *S. aureus* growth in tryptic soy broth (TSB) by 92%. When added to tunicamycin, the combination of sub-MIC tunicamycin and solvated lignin inhibited *S. aureus* growth by greater than 99.9%. Data represent the average of n=3 biological replicates, error bars represent SEM. *p=0.05, p<0.001 (Mann-Whitney Rank Sum Test) (FIG. 13**).

Figure 14:
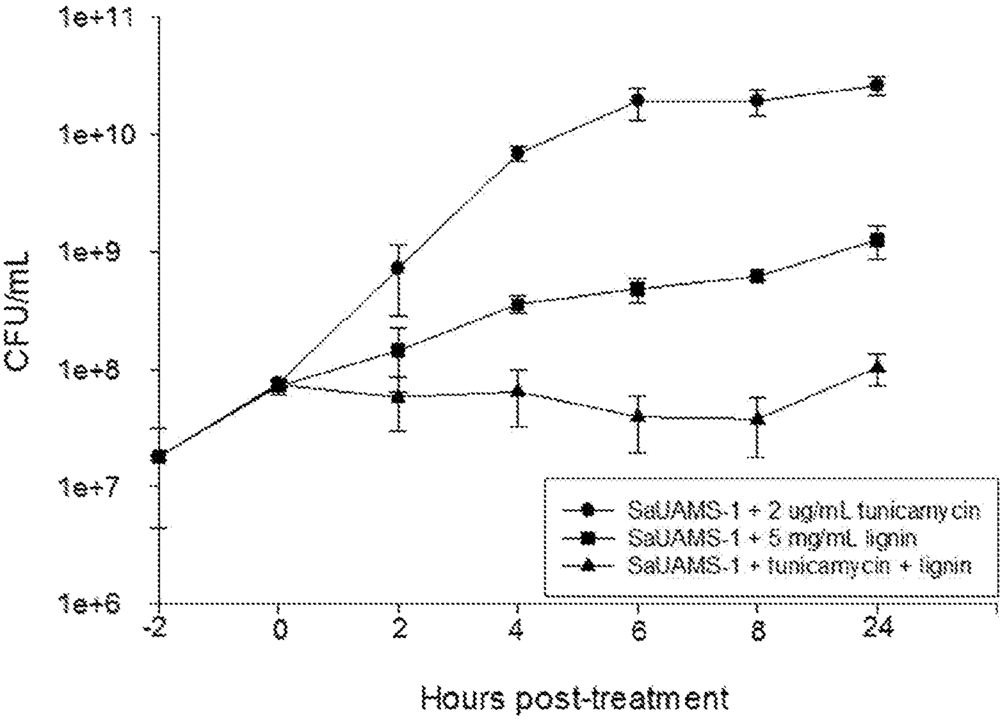
FIG. 14. Graph illustrating inhibition of *S. aureus* UAMS-1 in the presence of sub-MIC tunicamycin, lignin, or sub-MIC tunicamycin plus lignin (added during exponential growth). Statistically significant differences between all groups were observed from $T_2$-$T_{24}$ (n=3 biological replicates, p≤0.05). Error bars represent standard deviation of n=3 biological replicates across two independent experiments.

Tunicamycin susceptibility curve: Overnight cultures of *S. aureus* UAMS-1 were diluted to $OD_{600}$=0.025 in 19 mL fresh tryptic soy broth (TSB), then grown for 2 hours at 37° C. and 250 rpm. At this time point ("To"), one mL of 1 M MOPS containing either tunicamycin (40 μg), lignin (100 mg), or tunicamycin (40 μg)+lignin (100 mg) was added to separate cultures (final concentrations: 50 mM MOPS, 2 μg/mL tunicamycin (sub-MIC), 5 mg/mL lignin). Colony forming units (CFU) were measured every two hours from $T_{-2}$-$T_8$, and $T_{24}$. Error bars represent standard deviation of n=3 biological replicates across two independent experiments. Statistical differences between all three groups were analyzed with t-tests, which showed a significant difference between all groups from $T_2$-$T_{24}$ ($p \leq 0.05$). The results, shown in FIG. 14-15, demonstrate that solubilized lignin can be used as an adjuvant to tunicamycin antibiotic therapy.

Figure 15:
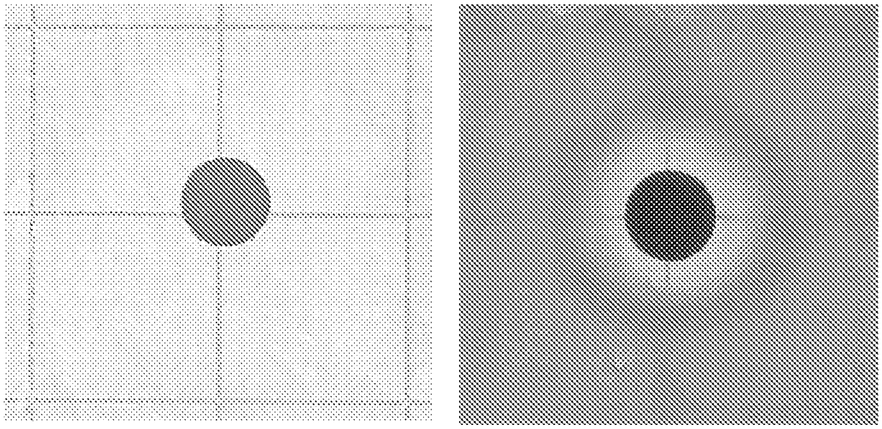
FIG. 15. Tunicamycin disk diffusion assay. Exponentially growing *S. aureus* UAMS-1 cultures were spread across tryptic soy agar plates containing 50 mM MOPS (left) and 50 mM MOPS+5 mg/mL lignin (right). Paper disks containing 2 μg tunicamycin were placed in the center. Growth to the edge of a disk indicates tolerance of the antibiotic (left), while a clear zone of no growth indicates susceptibility (right). Images are representative of n≥3 biological replicates.

Tunicamycin disk diffusion assay: *S. aureus* UAMS-1 cultures were prepared by inoculating separate 15-mL culture tubes containing 3 mL sterile 3% (w/v) TSB with a single colony and incubated 14-16 h at 37° C. while shaking at 250 rpm. Fresh 50-mL cultures with an initial $OD_{600}$=0.025 were prepared and incubated for 2 h at 37° C. and 250 rpm. Cells were collected by centrifugation at 4,500 rpm and resuspended in 500 μL sterile Hank's Balanced Salt Solution (HBSS; Corning, Corning, NY). A 250-μL aliquot from each culture was pipetted onto a TSA plate containing 50 mM MOPS and a TSA plate containing 50 mM MOPS and 5 mg/mL lignin. Cells were spread across the plates with sterile glass beads and the plates were left open to dry in a clean laminar-flow hood for 10-15 min. Tunicamycin (2 μg) was dropped on blank paper disks (Oxoid, Basingstoke, UK) then placed on the agar and incubated for 24 h at 37° C.; plates were visually inspected for zones of clearance (no growth) around the disks indicating susceptibility to tunicamycin. No clearance zone was observed on the MOPS plate. In contract, a clearance zone was observed in the MOPS+5 mg/ml lignin plate (FIG. 15). Three biological replicates were analyzed.

Example 12. Propidium iodide staining and quantification. *S. aureus* UAMS-1 was streaked onto a TSA plate and incubated for 24 h at 37° C. Isolated, similarly sized colonies were added to 5 mL TSB with 50 mM MOPS±5 mg/mL sugarcane lignin in separate 50 mL Erlenmeyer flasks, then grown for 24 h at 37° C. and 250 rpm. Cells were pelleted by centrifugation (5 m at 13,400 rpm), washed with 0.9% (w/v) NaCl solution, then resuspended in 0.9% NaCl containing 1.5 μg/mL propidium iodide (ThermoFisher Scientific, Waltham, MA) and placed in the dark for 30 min. at room temperature. Cells were pelleted and washed with 0.9% NaCl, then pelleted and resuspended in 0.9% NaCl. The fluorescence (495 nm excitation/635 nm emission) and $OD_{600}$ of triplicate biological samples of 100 μL from each treatment were read in an optically clear 96-well plate (Corning, Corning, NY) using area scanning on a Biotek Cytation3 plate reader (Winooski, VT). Untreated and lignin-treated cultures not stained with propidium iodide (PI) were measured concurrently with untreated and lignin-treated PI-stained cultures. Relative fluorescent unit (RFU) values obtained from unstained cultures were subtracted from those obtained from PI-stained cultures; the corrected RFU values were then normalized to the $OD_{600}$ of each well.

Flow cytometry and analysis. Cells remaining from the PI staining experiment were analyzed with a Becton Dickinson (BD) Accuri C6 flow cytometer (Franklin Lakes, NJ). At least 500,000 events were measured ungated from each sample, and data were exported as .fcs files to FlowJo (Ashland, OR) for analysis and graphical visualization. Gating was applied and measured events were displayed in pseudo-colored density heatmaps, where population densities were displayed from lowest to highest, indicating relative proportions of cell populations in untreated and lignin-treated cultures. Three biological replicates were analyzed.

Figure 18:
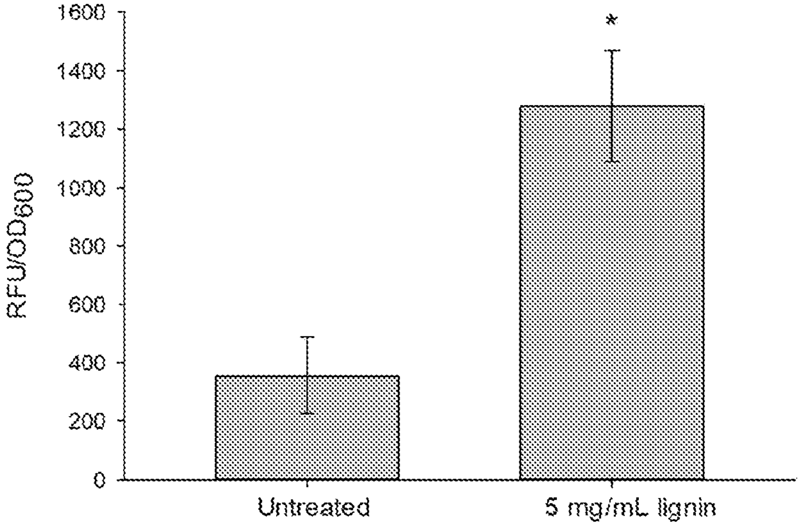
FIG. 18. Graph illustrating relative membrane damage of *S. aureus* UAMS-1 cells treated with 5 mg/ml lignin as evidenced by propidium iodide fluorescence (relative fluorescence units, RFUs) standardized to the cell optical density of each sample (Y axis). * indicates P<0.001; n=3 biological replicates; Error bars represent the standard deviation.
Figure 19:
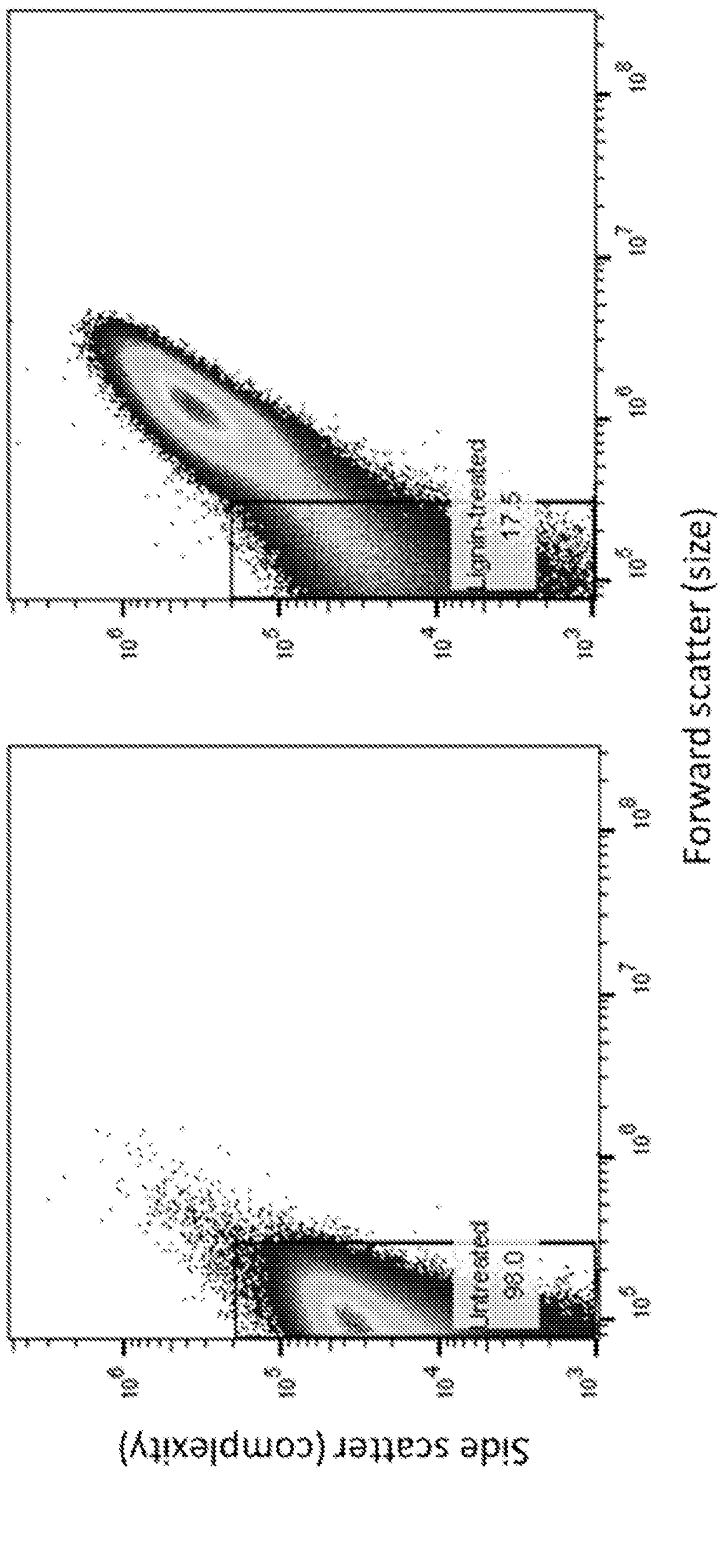
FIG. 19. Flow cytometry analysis of untreated cultures (left) and cultures treated with lignin derived from sugarcane bagasse (right). Cell population densities, where cell densities are displayed from lowest to highest, illustrate a substantial shift in cell populations towards greater size (horizontal axis) and complexity (vertical axis) in lignin-treated cultures. Smaller, less complex cell clusters make up 98% of the population in the untreated sample. Only 17.5% of lignin-treated cells remained within that range, while the rest became substantially larger and more complex indicating abnormal cell aggregation.

Results: The results demonstrated that lignin-treated cells take up approximately four-fold more PI than untreated cells, indicating a significantly higher level of membrane damage and/or cell death from lignin treatment alone (FIG. 18). Furthermore, flow cytometry analysis of lignin-treated cultures demonstrated the formation of large, complex cell clusters not seen in untreated cultures (FIG. 19), suggesting that cell division may have been altered. Lignin may disrupt transmembrane signal transduction by damaging the membrane itself. These results are the first to demonstrate the antibacterial activity of aqueously solvated, underivatized lignin against a clinical *S. aureus* strain, and to demonstrate antibacterial synergy between unmodified lignin and a cell wall-targeting antibiotic.

Example 13. Sensitivity of *S. agalactiae* and *S. uberis* to β-lactams and lignin. Type strains of *S. agalactiae* and *S. uberis* Diemhofer (NCTC 8181 and NCTC 3858, respectively) were obtained from the American Type Culture Collection (ATCC) as lyophilized pellets. Cells were revived by resuspension in 5 mL Todd Hewitt broth (THB, 3% w/v) and static incubation for 24 h at 37° C. Culture $OD_{600}$ was measured and the volume to achieve $OD_{600}$=0.025 was added to 50 mL fresh THB in 250 mL Erlenmeyer flasks and grown for 2 hours; *S. agalactiae* cultures were supplemented with 1 μM hemin and 10 μM menaquinone and grown at 37° C. and 200 rpm, while *S. uberis* was grown statically at 37° C. Cultures were centrifuged at 4500 rpm for 10 minutes. Due to differences in pellet sizes, *S. agalactiae* pellets were resuspended in 1 mL Hank's Balanced Salt Solution (HBSS), and *S. uberis* pellets were resuspended in 400 μL HBSS in order to normalize the $OD_{600}$ of the two cell suspensions. Exponentially growing *S. agalactiae* (100 μL aliquot) was spread on Todd Hewitt agar (THA, 3% THB+1.5% agar, 1 μM hemin, 10 μM menaquinone, and 50 mM MOPS (pH 7.2±0.05)±5 mg/mL sugarcane lignin) with sterile glass beads, while Exponentially growing *S. uberis* (200 μL) was spread on THA+50 mM MOPS±5 mg/mL lignin. Paper disks containing 10 μg penicillin, 10 μg ampicillin, and 30 μg amoxicillin+clavulanic acid (Oxoid, Basingstoke, UK) were placed on the agar, then incubated for 24 h at 37° C. Plates were inspected for zones of clearance around the disks indicating susceptibility.

Figure 16:
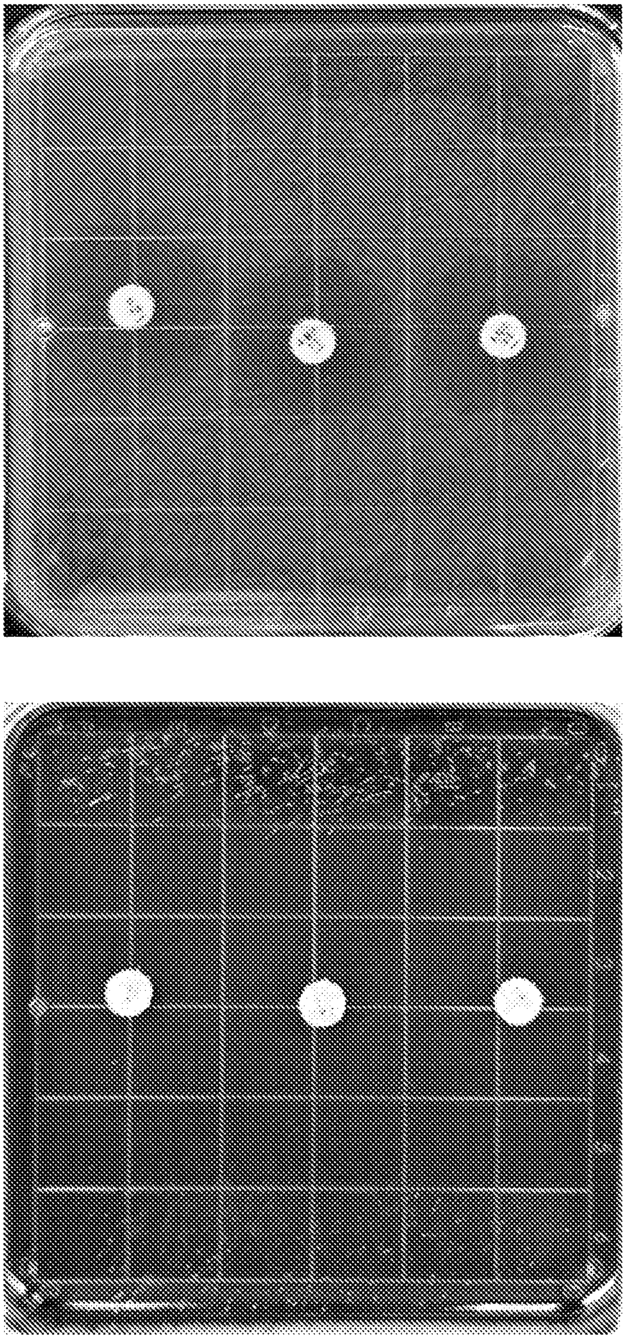
FIG. 16. *Streptococcus agalactiae* β-lactam disk diffusion susceptibility test. A. (top) In TSA without lignin, *S. agalactiae* is moderately sensitive to (left to right) penicillin, ampicillin, and amoxicillin+clavulanic acid. B. (bottom) In the presence of 5 mg/mL lignin, *S. agalactiae* is highly sensitive to (left to right) penicillin, ampicillin, and amoxicillin+clavulanic acid. Images representative of n=2 biological replicates.
Figure 17:
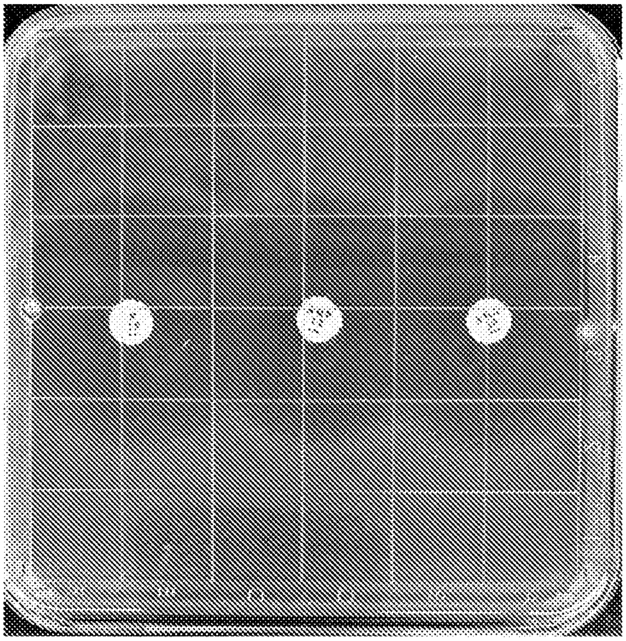
FIG. 17. *Streptococcus uberis* β-lactam disk diffusion susceptibility test. A. (top) In TSA without lignin, *S. uberis* is moderately sensitive to (left to right) penicillin, ampicillin, and amoxicillin+clavulanic acid. B. (bottom) In the presence of 5 mg/mL lignin, *S. uberis* is highly sensitive to (left to right) penicillin, ampicillin, and amoxicillin+clavulanic acid. Images representative of n=2 biological replicates.
Figure 17:
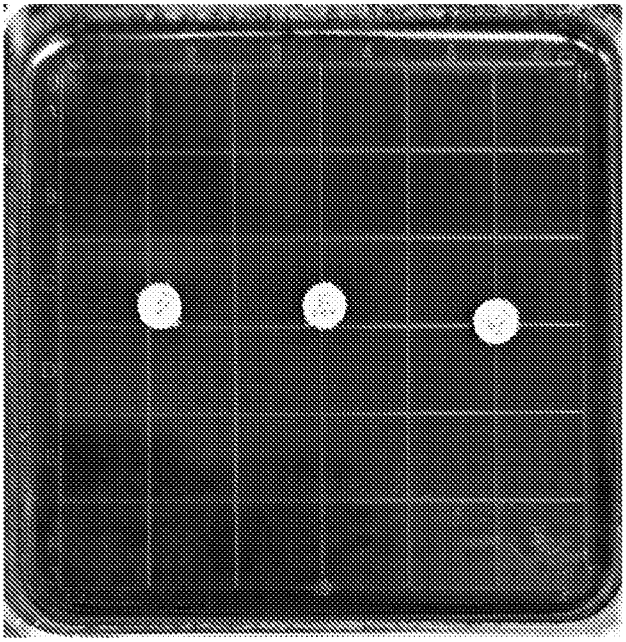

On control plates without lignin, *S. agalactiae* and *S. uberis* attained lawn-style growth punctuated by clearance zones surrounding the antibiotic disks. Based on the clearance zones, both species displayed some susceptibility to penicillin, ampicillin, and amoxicillin+clavulanic acid. The clearance zones on the plates with *S. agalactiae* were smaller in diameter compared to the plates with *S. uberis*, indicating the *S. agalactiae* was less susceptible to the antibiotics. (FIGS. 16A and 17A). Surprisingly, growth of both species was nearly completely inhibited in the presence of lignin (FIGS. 16B and 17B). The growth of both species was inhibited so severely in the presence of lignin that the only growth observed was on the outermost edges of the plates, furthest away from the disks with antibiotics. In the case of *S. uberis*, growth was nearly undetectable and appeared only as a slight haze. These observations, combined with our prior results on *S. aureus*, indicate that the presence of lignin alone is substantially more inhibitory against *S. agalactiae* and *S. uberis* than against *S. aureus*. Moreover, in the presence of lignin, sensitivity to β-lactams was dramatically increased. These results indicate that the described solubilized lignin can be utilized as an adjuvant to antibiotic therapy. In particular, the described aqueous lignin can be utilized as an adjuvant to β-lactam antibiotic therapy. Such therapy is useful in a number of applications, including, but not limited to, the dairy industry.

Example 14. Regenerable solvent-antisolvent system for the removal of lignin from lignocellulose. The process of separating lignin from cellulose and hemicellulose is an expensive step in the lignocellulose biorefining process and involves potentially toxic compounds. Ionic liquid solvents, including deep eutectic solvents (IL/DES), can be used to delignify lignocellulose and have the advantage of being regenerated and reused by addition of an antisolvent. Although they are expensive and often toxic, IL/DES are generally considered as being superior to older methods of delignification. 3-(Cyclohexylamino)-1-propanesulfonic acid (CAPS, pKa 10.4), and 4-(cyclohexylamino)-1-butanesulfonic acid (CABS, pKa 10.7) may be suitable alternatives to IL/DES due to their lower cost, lower toxicity, and ease of regeneration.

CAPS was prepared at 1 M concentration and adjusted to pH 9.6 with NaOH pellets (final concentration 0.175 M NaOH). The pH-adjusted CAPS solution (40 mL) was added to a 1000-mL round-bottom flask and tared to zero on a weighing scale. Washed, lyophilized, shredded sorghum bagasse was weighed in approximately 1 g amounts, added to the flask, then re-weighed to obtain the actual mass of bagasse in the flask. The flask was attached to a rotary evaporator (R-124; Büchi, New Castle, DE), partially submerged in a water bath set at 45° C., and rotated at 240 rpm for 5 min. The mixture was filtered through a Buchner funnel lined with a 0.45-μm poly(vinylidene difluoride) (PVDF) filter and the round-bottom flask was rinsed with 60 mL absolute ethanol. The ethanol was poured into the Buchner funnel containing the insoluble portion of bagasse, followed by another 300 mL absolute ethanol. The insoluble portion was weighed after complete drying in a 60° C. oven, and the mass removed (%) was calculated as "100−([insoluble portion/bagasse]×100)". The filtrate, containing lignin, was stirred to ensure complete mixing with ethanol, then poured into 50 mL Oak Ridge-style tubes (Nalgene, Rochester, NY) and centrifuged (Avanti® J-26 XP; Beckman-Coulter, Brea, CA) at 20,000 rpm for 15 min. Ethanol acted as an antisolvent to facilitate precipitation of the lignin. The supernatant was poured back into the round-bottom flask and attached to the rotary evaporator, and ethanol was removed under vacuum at 45° C. The remaining volume was used to repeat the delignification procedure.

Treatment of sorghum bagasse with CAPS (pH 9.6) removed approximately 25% of its mass. This mass is expected to be lignin. The process was determined to be regenerable after it was repeated without additional input of water, CAPS, or NaOH. The data indicates CAPS buffer (pH 9.6) was effective at removing biomass from lignocellulose. The biomass is expected to be lignin. It is further predicted that the process is scalable and may be indefinitely regenerable provided that the buffer concentration and pH are maintained.

TABLE 4

| Delignification of sorghum bagasse with CAPS (pH 9.6). Values are presented as the sample mean ± standard deviation from two experiments. | | |
|---|---|---|
| Bagasse (g) | Insoluble portion (g) | Mass removed (%) |
| 1.11 ± 0.02 | 0.835 ± 0.05 | 25 ± 2 |

Example 15. Lignin compositional analysis. The composition of phenolic subunits from lignin used in solvation and antibacterial experiments was analyzed by pyrolysis-gas chromatography-mass spectrometry (Py-GC-MS). In addition, the lignin was analyzed to determine if sugars or other by-products of NaOH hydrolysis were present in lignin samples.

Small solid samples (~100 ng) of (1) freeze-dried sorghum bagasse, (2) alkaline lignin extracted from sorghum bagasse, (3) insoluble residue remaining after alkaline lignin extraction from sorghum bagasse and (4) dilute acid sugarcane lignin were placed in individual quartz sample vials. Each sample was subjected to Py-GC-MS by inserting the vial in an aluminum sample probe that was lowered in a Bruker 1079 programmable temperature vaporization (PTV) inlet of a Bruker Scion 456 gas chromatograph (Bremen, Germany). The GC was equipped with a Restek Rtx®1701 column (30 m, 0.25 mm i.d., 0.25 μm film thickness; Restek Corp., Bellefonte, PA), which was connected to a Bruker Scion triple quadrupole mass spectrometer. The PTV injector was initially set at 100° C. and quickly ramped up to 450° C. under a helium pressure of 20 psi. The split ratio was 1:100. The pyrolysis fragments were led on the column with an initial temperature of 70° C., which was maintained for 3.5 min. The temperature was then increased to 140° C. (5° C. $min^{-1}$), 220° C. (2.5° C. $min^{-1}$), and 270° C. (12.5° C. $min^{-1}$) with a 2.5 min. final hold. The transfer line was maintained at 250° C. Electron impact ionization was used with 70 eV electrons. The m/z range was set from 50-225, with a scan speed of 500 ms. Data were analyzed in Bruker Daltonics MS WorkStation software v. 8.2.1 and fragments were identified using a combination of the NIST mass spectral library (2014) and data from Ralph and Hatfield (J. Agric. Food Chem., 1991, 39(8), 1426-37).

FIG. 20 contains the chromatograms obtained from the dilute acid sugarcane lignin (A), alkaline sorghum lignin (B), sorghum bagasse (C), and the sorghum bagasse following lignin extraction (D). The peaks have been labeled with numbers (phenolic compounds) and letters (other compounds). The identities of those compounds are listed in FIG. 20E. The chromatograms obtained from the two lignin samples (A and B) only contain peaks representing phenolic compounds, confirming that they are lignins that contain no detectable contamination with polysaccharides or other small molecules. The two lignin samples look overall similar, with small differences in the relative peak heights (e.g., peaks 7 and 8) that will reflect differences in species (sugarcane versus sorghum), age of the plants at the time of harvest, and extraction method. The chromatogram obtained from the residue remaining after the extraction of lignin from the sorghum bagasse (D) contains peaks derived from polysaccharides (indicated by letters), and even though there are some peaks representing phenolic compounds (numbered), they are proportionally small. As expected, the chromatogram obtained for the sorghum bagasse contains peaks present in both the lignin (B) and the residue (D)

These results indicate the lignin samples used for solvation and antibacterial experiments were functionally lacking sugars and by-products from NaOH extraction, thus providing high-purity lignin samples.

Example 16. Lignin cytotoxicity assay. The effects of lignin on human cells was analyzed. The ability to solvate lignin in aqueous solutions provided the opportunity to examine the effects of lignin against human cells, such as normal human epidermal keratinocytes (NHEK) (Sigma-Aldrich, C-12008), cells which are reported to make up 90% of the epidermis.

Receiving and storing proliferating cells can be performed as follows.

1. Immediately upon receipt, place culture vessel in 37° C. 5% $CO_2$ incubator for 3 hours to allow cells to recover from transport.
2. Carefully open vessel, rinse lid with 70% ethanol (let air dry) and remove transport medium. Replace with 10 mL Keratinocyte Growth Medium 2 (Sigma-Aldrich, C-20011).
3. Replace lid, open ½-turn and place vessel in 37° C. 5% $CO_2$ incubator. Cells are checked daily under a microscope until they have reached 70-90% confluency. Subcultures are then prepared.

Cell detachment and sub-culture with lignin.

1. Allow PromoCell Detach Kit containing HEPES BSS wash buffer, trypsin, and trypsin neutralizing solution (Sigma-Aldrich, C-41200) to reach room temperature. Add 100 μL HEPES BSS Solution per $cm^2$ of vessel surface (e.g., 7.5 mL) to wash the cells by agitating vessel gently for 15 seconds.
2. Remove HEPES BSS, replace with 100 μL trypsin EDTA per $cm^2$ (e.g., 7.5 mL) at room temperature, and gently agitate vessel to detach cells.
3. Add 7.5 mL trypsin neutralizing solution to the vessel and gently agitate. Pipette cell suspension into 15 mL centrifuge tube and spin down cells at 1400 rpm for 3 min.
4. Discard supernatant, resuspend cells in 1 mL Keratinocyte Growth Medium 2+50 mM MOPS±5 mg/mL sugarcane lignin. Aliquot 100 μL from each sample in quadruplicate to a 96-well plate, then incubate for 24 hours at 37° C. 5% $CO_2$.

WST-8 Cytotoxicity Assay

1. Remove growth media. Prepare 10% cell proliferation reagent (WST-8) solution in sterile water. Wash cells with 100 μL/well HEPES BSS, then replace with 100 μL cell proliferation reagent solution and incubate at 37° C. 5% $CO_2$ for 1 hour.
2. Measure absorbance (450 nm) of media-only blanks, control (untreated), and lignin-treated samples, then subtract blank $Abs_{450}$ from the cell samples.

Other cell types can be readily examined in the above protocol. Variations in conditions may be appropriated for different cells types.

Viability of lignin-treated human (or mammalian) cells, such as normal human epidermal keratinocytes cells, is determined relative to human (or mammalian) cells, such as normal human epidermal keratinocytes cells, not treated with lignin. Lignin-treatment is not expected to reduced viability of the human (or mammalian) cells, including normal human epidermal keratinocytes cells. No significant reduction in viability compared to control cells indicates that application of a solution containing GB-solvated lignin is not harmful towards human (or mammalian) cells and that lignin alone or contained in lignin-based polymers and materials can be used with or on human and/or mammalian tissue, such as epidermal tissue.

Example 17. *Staphylococcus aureus* kill curve with alkaline sorghum lignin (ASL). Antibacterial activity of lignin extracted from a source other than biorefinery residues was analyzed. Sorghum lignin was extracted in alkaline solution according to Example 3 and solvated in MOPS buffer according to Example 4. *S. aureus* UAMS-1 cultures were prepared according to Example 11 but without tunicamycin. At $T_0$, UAMS-1-1 and UAMS-1-2 were treated with 50 mM MOPS and UAMS-1-1L and UAMS-1-2L were treated with 50 mM MOPS+5 mg/mL ASL. Colony forming units (CFU) were enumerated in triplicate from each time point, and the % inhibition after 24 h was calculated by "100−(treated/untreated)" at $T_{24}$. Two biological replicates were analyzed.

TABLE 5

Inhibition of *S. aureus* UAMS-1 growth in 50 mM MOPS (UAMS-1-1 and UAMS-1-2) or 50 mM MOPS ± alkaline sorghum lignin (UAMS-1-1L and UAMS-1-2L). Values are displayed as the average of triplicate CFU measurements

| | $T_{-2}$ | $T_0$ | $T_2$ | $T_4$ | $T_6$ | $T_8$ | $T_{24}$ | % inhibition |
|---|---|---|---|---|---|---|---|---|
| UAMS-1-1 | 1.66E+07 | 4.33E+07 | 1.13E+09 | 5.43E+09 | 6.86E+09 | 8.26E+09 | 1.73E+10 | |
| UAMS-1-2 | 1.83E+07 | 4.00E+07 | 1.63E+09 | 5.13E+09 | 6.66E+09 | 8.70E+09 | 1.93E+10 | |
| UAMS-1-1L | | 3.30E+07 | 3.66E+07 | 6.40E+07 | 1.06E+07 | 2.03E+07 | 2.50E+08 | 99.99 |
| UAMS-1-2L | | 3.83E+07 | 5.40E+07 | 8.50E+07 | 1.26E+07 | 1.70E+07 | 2.30E+08 | 99.99 |

*S. aureus* UAMS-1 growth is inhibited >99% when treated with ASL, demonstrating the antibacterial activity of ASL lignin and lignin from sources other than biorefinery residues.

Example 18. *S. aureus* cell wall morphology in the presence and absence of lignin. The effects of lignin on *S. aureus* cell wall morphology and biosynthesis was analyzed. *S. aureus* UAMS-1 cultures were prepared according to Example 4, but without tunicamycin addition at $T_0$. At two hours post-treatment ($T_2$), 100 μL aliquots of untreated and lignin-treated cells were washed with fresh 50 mM MOPS (pH=7.2), then resuspended in 4% paraformaldehyde and 2.5% glutaraldehyde in 0.1 M cacodylate buffer (pH=7.24). Fixed cells were processed with a Pelco BioWave Pro laboratory microwave (Ted Pella, Redding, CA) and SBT digital orbital shaker (Southwest Science, Trenton, NJ). Cells were washed in 0.1 M cacodylate buffer (pH=7.24), encapsulated in buffered 3% (w/v) agarose, post-stained with buffered 2% (v/v) osmium tetroxide, and water washed. Samples were dehydrated in a graded ethanol series of 25%-100% (v/v), followed by 100% anhydrous acetone. Dehydrated specimens were infiltrated in 30%, 50%, 70% and 100% Embed/Araldite epoxy resin with Z6040 embedding primer (Electron Microscopy Sciences, Hatfield, PA), and cured at 60° C. for at least 48 hours. Semi-thick sections of 500 nm were stained with toluidine blue. Ultra-thin sections of 100-120 nm were collected on 100 mesh copper-coated Formvar grids and post-stained with 2% (v/v) aqueous uranyl acetate and Reynold's lead citrate. Sections were examined with FEI Tecnai G2 Spirit Twin TEM (FEI Corp., Hillsboro, OR) and digital images were acquired with a Gatan UltraScan 2 k×2 k camera and Digital Micrograph software (Gatan Inc., Pleasanton, CA).

Examination of images from lignin-treated cells indicated that cells developed an abnormally thick cell wall with a rough "hairy" appearance (see FIG. 21). Cells appeared to be able to grow and divide, but do not always undergo complete separation when growing in the presence of lignin, thus giving rise to the large cell clusters noted in previous experiments. The results suggest that lignin impairs normal cell division and/or cell wall metabolism in *S. aureus.*

The invention claimed is:

1. An aqueous lignin solution comprising lignin solvated in a Good's buffer solution at about pH 6.5 to about pH 7.5, wherein the Good's buffer contains a zwitterionic N-substituted aminosulfonic acid moiety, and wherein the lignin is from an alkaline extraction process and is not chemically derivatized with any anionic moieties.

2. The aqueous lignin solution of claim 1, wherein the Good's buffer in the Good's buffer solution is selected from the group consisting of:

3-morpholinopropane-1-sulfonic acid (MOPS),
4-(2-hydroxyethyl)-1-piperazinepropanesulfonic acid (EPPS),
3-(cyclohexylamino)-1-propanesulfonic acid (CAPS),
2-[4-(2-hydroxyethyl) piperazin-1-yl] sulfonic acid (HEPES),
N-cyclohexyl-2-aminoethanesulfonic acid (CHES),
2-(N-morpholino) ethanesulfonic acid (MES),
N-(2-Acetamido)-2-aminoethanesulfonic acid (ACES),
N-(1,1-Dimethyl-2-hydroxyethyl)-3-amino-2-hydroxypropanesulfonic acid (AMPSO),
N,N-Bis(2-hydroxyethyl)-2-aminoethanesulfonic acid (BES),
N-cyclohexyl-3-aminobutanesulfonic acid (CABS),
N-cyclohexyl-2-hydroxyl3-aminopropanesulfonic acid (CAPSO),
3-(N,N-Bis[2-hydroxyethyl] amino)-2-hydroxypropanesulfonic acid (DIPSO),
N-(2-Hydroxyethyl) piperazine-N'-(4-butanesulfonic acid) (HEPBS),
3-[4-(2-Hydroxyethyl)-1-piperazinyl] propanesulfonic acid (HEPPS),
4-(2-Hydroxyethyl) piperazine-1-(2-hydroxypropanesulfonic acid) (HEPPSO),
4-Morpholinobutanesulfonic acid (MOBS),
β-Hydroxy-4-morpholinepropanesulfonic acid (MOPSO),
1,4-Piperazinediethanesulfonic acid (PIPES),
Piperazine-N,N'-bis(2-hydroxypropanesulfonic acid) (POPSO),
N-[Tris(hydroxymethyl)methyl]-3-aminobutanesulfonic acid (TABS),
N-[Tris(hydroxymethyl)methyl]-3-aminopropanesulfonic acid (TAPS),
2-Hydroxy-3-[tris(hydroxymethyl)methylamino]-1-propanesulfonic acid (TAPSO), and
2-[(2-Hydroxy-1,1-bis(hydroxymethyl)ethyl)amino] ethanesulfonic acid (TES).

3. The aqueous lignin solution of claim 1, wherein the concentration of lignin in the aqueous lignin solution is ≥100 mg/mL.

4. The aqueous lignin solution of claim 1, wherein the concentration of the Good's buffer in the Good's buffer solution is 1 mM to 1 M.

5. The aqueous lignin solution of claim 1, wherein the lignin is:

(a) a gymnosperm lignin, (b) an angiosperm lignin, or (c) a grass lignin.

6. A method for preparing an aqueous lignin solution, comprising:

(a) obtaining lignin from an alkaline extraction process wherein the lignin is not chemically derivatized with any anionic moieties, and (b) combining the lignin with a Good's buffer in an aqueous solution, wherein the Good's buffer contains a zwitterionic N-substituted aminosulfonic moiety and has a pH of 6.5-7.5, thereby solvating the lignin.

7. The method of claim 6, wherein the obtaining lignin in step (a) comprises one of the following steps:

(i) obtaining lignin-containing residues produced by a lignocellulosic biorefinery;

(ii) obtaining lignin from liquefaction plus simultaneous saccharification and co-fermentation of phosphoric acid-pretreated plant material; or (iii obtaining lignin from non-pretreated plant bagasse with sodium hydroxide.

8. The method of claim 6, wherein the obtaining lignin in step (a) comprises obtaining lignin from one or more of: a gymnosperm, an angiosperm dicot, a grass, a plant bagasse, a sorghum, a sugarcane, a wheat straw, a sorghum bagasse, and a sugarcane bagasse.

9. The method of claim 6, wherein the Good's buffer is selected from the group consisting of:

3-morpholinopropane-1-sulfonic acid (MOPS), 4-(2-hydroxyethyl)-1-piperazinepropanesulfonic acid (EPPS), 3-(cyclohexylamino)-1-propanesulfonic acid (CAPS), 2-[4-(2-hydroxyethyl) piperazin-1-yl] sulfonic acid (HEPES), N-cyclohexyl-2-aminoethanesulfonic acid (CHES), 2-(N-morpholino) ethanesulfonic acid (MES), N-(2-Acetamido)-2-aminoethanesulfonic acid (ACES), N-(1,1-Dimethyl-2-hydroxyethyl)-3-amino-2-hydroxypropanesulfonic acid (AMPSO), N,N-bis(2-hydroxyethyl)-2-aminoethanesulfonic acid (BES), N-cyclohexyl-3-aminobutanesulfonic acid (CABS), N-cyclohexyl-2-hydroxyl3-aminopropanesulfonic acid (CAPSO), 3-(N,N-bis[2-hydroxyethyl] amino)-2-hydroxypropanesulfonic acid (DIPSO), N-(2-Hydroxyethyl) piperazine-N'-(4-butanesulfonic acid) (HEPBS), 3-[4-(2-Hydroxyethyl)-1-piperazinyl] propanesulfonic acid (HEPPS), 4-(2-Hydroxyethyl) piperazine-1-(2-hydroxypropanesulfonic acid) (HEPPSO), 4-Morpholinobutanesulfonic acid (MOBS), β-Hydroxy-4-morpholinepropanesulfonic acid (MOPSO), 1,4-Piperazinediethanesulfonic acid (PIPES), Piperazine-N,N'-bis(2-hydroxypropanesulfonic acid) (POPSO), N-[Tris(hydroxymethyl)methyl]-3-aminobutanesulfonic acid (TABS), N-[Tris(hydroxymethyl)methyl]-3-aminopropanesulfonic acid (TAPS), 2-Hydroxy-3-[tris(hydroxymethyl)methylamino]-1-propanesulfonic acid (TAPSO), and 2-[(2-Hydroxy-1,1-bis(hydroxymethyl)ethyl)amino] ethanesulfonic acid (TES).

10. The method of claim 6, wherein the lignin is solvated in the Good's buffer solution at a concentration of ≥100 mg/mL.

11. The method of claim 6, wherein the concentration of the Good's buffer in the Good's buffer solution is 1 mM to 1 M.

12. The method of claim 6, wherein solvating the lignin in the Good's buffer solution comprises combining the lignin with the Good's buffer solution at 18-25° C.

13. The method of claim 6, further comprising filter sterilizing the aqueous lignin solution.

14. An antimicrobial composition comprising the aqueous lignin solution of claim 1.

15. The antimicrobial composition of claim 14, further comprising an antibiotic, a β-lactam antibiotic, or tunicamycin.

16. The aqueous lignin solution of claim 1, for use in treating a microbial infection, wherein the microbial infection is a *Staphylococcus aureus* infection, a β-lactam-resistant *S. aureus* infection, a β-lactam-susceptible *S. aureus* infection, a methicillin-resistant *S. aureus* infection, a *Streptococcus uberis* infection, or a *Streptococcus agalactiae* infection.

17. The aqueous lignin solution of claim 16, wherein the aqueous lignin solution further comprises an antibiotic, a β-lactam, or a tunicamycin.

18. The aqueous lignin solution of claim 1, for use in inhibiting bacterial growth, wherein the bacteria comprises *Staphylococcus aureus, Streptococcus uberis, Streptococcus agalactiae*, β-lactam-resistant *S. aureus*, β-lactam-susceptible *S. aureus*, or methicillin-resistant *S. aureus.*

19. A process of delignifying lignocellulose comprising: adding a Good's buffer containing a zwitterionic N-substituted aminosulfonic moiety at pH 5.5-11.5 to the lignocellulose to form a mixture, incubating the mixture for at least 5 minutes to solvate lignin in the mixture, filtering the mixture to remove solvated lignin from insoluble material, precipitating lignin with an anti-solvent, collecting precipitated lignin, and removing the anti-solvent to regenerate the GB, wherein the regenerated GB is available to repeat one or more additional delignification procedures.

20. The method of claim 6, where combining the lignin with a Good's buffer comprises incubating the lignin with the Good's buffer for less than about 120 minutes.

* * * * *